(12) United States Patent
Zayed et al.

(10) Patent No.: US 12,226,575 B2
(45) Date of Patent: Feb. 18, 2025

(54) AIRWAY MANAGEMENT SYSTEM WITH SELECTIVELY PRESSURIZED VALVE

(71) Applicants: Mohamed Zayed, St. Louis, MO (US); Zahid Iqbal, St. Louis, MO (US); Jin Vivian Lee, St. Louis, MO (US)

(72) Inventors: Mohamed Zayed, St. Louis, MO (US); Zahid Iqbal, St. Louis, MO (US); Jin Vivian Lee, St. Louis, MO (US)

(73) Assignee: Washington University, St. Louis, MO (US)

(*) Notice: Subject to any disclaimer, the term of this patent is extended or adjusted under 35 U.S.C. 154(b) by 666 days.

(21) Appl. No.: 17/397,703

(22) Filed: Aug. 9, 2021

(65) Prior Publication Data

US 2022/0040429 A1 Feb. 10, 2022

Related U.S. Application Data

(60) Provisional application No. 63/062,885, filed on Aug. 7, 2020.

(51) Int. Cl.
| | | |
|---|---|---|
| *A61M 16/04* | (2006.01) | |
| *A61M 16/06* | (2006.01) | |
| *A61M 16/10* | (2006.01) | |
| *A61M 16/20* | (2006.01) | |
| *A61B 1/00* | (2006.01) | |
| *A61B 1/267* | (2006.01) | |

(52) U.S. Cl.
CPC .... *A61M 16/0463* (2013.01); *A61M 16/0402* (2014.02); *A61M 16/045* (2014.02); *A61M 16/0461* (2013.01); *A61M 16/0488* (2013.01); *A61M 16/0605* (2014.02); *A61M 16/105* (2013.01); *A61M 16/208* (2013.01); *A61B 1/00082* (2013.01); *A61B 1/267* (2013.01)

(58) Field of Classification Search
CPC ..................................................... A61M 16/04
See application file for complete search history.

(56) References Cited

U.S. PATENT DOCUMENTS

| | | | | |
|---|---|---|---|---|
| 3,538,917 A | * | 11/1970 | Selker | A61B 17/122 251/5 |
| 3,848,605 A | * | 11/1974 | Harautuneian | A61M 16/04 604/100.01 |
| 4,848,334 A | * | 7/1989 | Bellm | A61M 16/06 D24/110.4 |
| 4,877,025 A | * | 10/1989 | Hanson | A61M 16/0468 128/207.15 |
| 4,958,707 A | * | 9/1990 | Yoneda | B66B 1/3415 187/247 |
| 5,657,752 A | * | 8/1997 | Landis | A61M 16/0633 128/205.24 |
| 5,660,714 A | * | 8/1997 | Wittenbrink | B01J 23/755 585/737 |
| 5,694,929 A | * | 12/1997 | Christopher | A61M 16/0409 128/207.14 |

(Continued)

*Primary Examiner* — LaToya M Louis

(57) ABSTRACT

Devices, systems, and methods of facilitating airway management with reduced risk of release of droplets and aerosolized pathogens from the lungs of a patient are disclosed, including a bronchoscope adapter for an endotracheal tube, an endotracheal tube with integral bronchoscope adapter, an endotracheal intubation mask system, a laryngeal mask airway-specific mask system, and a quick-seal laryngeal mask airway-specific mask system.

20 Claims, 18 Drawing Sheets

(56) References Cited

U.S. PATENT DOCUMENTS

| | | | | |
|---|---|---|---|---|
| 5,772,609 A * | 6/1998 | Nguyen | | A61M 25/09 |
| | | | | 600/585 |
| 5,918,598 A * | 7/1999 | Belfer | | A41D 13/1192 |
| | | | | 128/206.25 |
| 6,468,291 B2 * | 10/2002 | Bates | | A61F 2/0108 |
| | | | | 604/164.13 |
| 6,860,270 B2 * | 3/2005 | Sniadach | | A61M 16/06 |
| | | | | 128/207.14 |
| 6,886,561 B2 * | 5/2005 | Bayron | | A61M 16/20 |
| | | | | 128/207.14 |
| 7,900,626 B2 * | 3/2011 | Daly | | A61M 16/08 |
| | | | | 128/914 |
| 8,550,084 B2 * | 10/2013 | Ng | | A61M 16/0622 |
| | | | | 128/206.28 |
| 9,694,150 B2 * | 7/2017 | Brain | | A61M 16/0493 |
| 9,889,265 B2 * | 2/2018 | Fischer, Jr | | A61B 1/2676 |
| 9,907,919 B2 * | 3/2018 | Dubach | | A61M 16/04 |
| 10,173,022 B1 * | 1/2019 | Zachar | | A61M 16/0447 |
| 10,729,866 B2 * | 8/2020 | Cook | | A61M 16/0434 |
| 10,842,962 B2 * | 11/2020 | Brain | | A61M 16/0488 |
| 11,369,547 B2 * | 6/2022 | Lyunni | | A61J 15/0042 |
| 2002/0069869 A1 * | 6/2002 | Farmer | | A61M 15/0086 |
| | | | | 128/203.29 |
| 2003/0047189 A1 * | 3/2003 | Kumar | | A61M 16/06 |
| | | | | 128/206.29 |
| 2004/0111069 A1 * | 6/2004 | Schaaf | | A61M 16/0459 |
| | | | | 604/284 |
| 2004/0163648 A1 * | 8/2004 | Burton | | A61M 16/0605 |
| | | | | 128/204.21 |
| 2008/0045781 A1 * | 2/2008 | Salama | | A61F 2/0013 |
| | | | | 600/29 |
| 2009/0139524 A1 * | 6/2009 | Esnouf | | A61M 16/06 |
| | | | | 128/205.13 |
| 2010/0147304 A1 * | 6/2010 | Burton | | A61B 5/6803 |
| | | | | 128/204.23 |
| 2013/0098367 A1 * | 4/2013 | Chen | | A61M 16/04 |
| | | | | 128/207.15 |
| 2013/0152936 A1 * | 6/2013 | Ho | | A61M 16/0816 |
| | | | | 128/205.25 |
| 2013/0247917 A1 * | 9/2013 | Brain | | A61M 16/0488 |
| | | | | 128/207.14 |
| 2015/0083121 A1 * | 3/2015 | Fisher | | A61M 16/0051 |
| | | | | 128/205.13 |
| 2015/0182714 A1 * | 7/2015 | Cook | | A61M 16/04 |
| | | | | 128/207.15 |
| 2019/0059708 A1 * | 2/2019 | Lei | | A61B 1/00119 |
| 2019/0060606 A1 * | 2/2019 | Vazales | | A61M 25/1002 |
| 2020/0046926 A1 * | 2/2020 | Kwok | | A61M 16/0409 |
| 2023/0330376 A1 * | 10/2023 | White | | A61M 16/0463 |

* cited by examiner

Patent valve

Sealed valve (hydrostatic pressure in wall of valve

AIRWAY MANAGEMENT SYSTEM WITH SELECTIVELY PRESSURIZED VALVE

CROSS-REFERENCE TO RELATED APPLICATIONS

This application claims priority from U.S. Provisional Application Ser. No. 63/062,885 filed on Aug. 7, 2020, which is incorporated herein by reference in its entirety.

STATEMENT REGARDING FEDERALLY SPONSORED RESEARCH OR DEVELOPMENT

Not applicable.

FIELD OF THE DISCLOSURE

The present disclosure generally relates to devices, systems, and methods of facilitating airway management with reduced risk of release of droplets and aerosolized pathogens from the lungs of a patient.

BACKGROUND OF THE DISCLOSURE

In the throes of a coronavirus pandemic, critically ill patients in the ICU often require positive pressure ventilation and oxygen delivery through an endotracheal (ET) tube, laryngeal mask airway (LMA), or bag mask valve (BMV). Although ET intubation is the gold standard for airway management, LMAs have proven to be valuable adjuncts, and in some instances, superior alternatives to the ET tube. LMAs are valuable in a wide variety of clinical settings due to their relative ease of use, versatility, high first insertion success rate, and low complication profile. Notably, LMAs are capable of rapidly establishing airways when traditional attempts to ventilate/oxygenate using facemask ventilation or ET tube placement are not possible.

Timely and appropriate management of COVID-related acute respiratory distress syndrome (ARDS) is hindered by the reluctance of providers to initiate early intubation or alternatives such as LMA ventilation. Critically ill COVID patients with high oxygen requirements often deteriorate rapidly and require mechanical ventilation within 1-3 days. Current recommendations are to maintain patients on continuous positive airway pressure (CPAP) for as long as possible using the lowest effective pressures (e.g. 5-10 cm H$_2$O); for patients with higher oxygen requirements, non-invasive modalities are recommended rather than proceeding directly to intubation. Respiratory care of COVID-positive patients may improve significantly with technologies that allow interchangeable use of an ET tube or LMA device within a closed system.

LMAs are especially important in resuscitation and field situations, where rapid stabilization and successful ventilation/oxygenation are critical to patient survival. In the out-of-hospital setting, LMA ventilation requires no expertise in mask ventilation or intubation; is proven to have faster and greater ventilation success for inexperienced clinicians; offers a wide variety of devices for use in nonstandard situations (e.g. in lateral or prone positions, immobilized head/neck); and can directly facilitate intubation without the use of direct laryngoscopy. Critically ill patients may benefit from the notable timesaving offered by LMA ventilation, by decreasing both the time to achieve insertion and the time to administration of indicated treatment/medications.

Commercially available bronchoscope adapters, ETTs, and LMAs do not provide for sealing against aerosolization and may potentially expose medical providers and other hospital personnel to the dispersion of aerosolized viral particles from the airways of patients with contagious airborne pathogens, such as aerosolized COVID-19 viral RNA. Consequently, these procedures require the usage of additional personal protective equipment (PPE), such as Powered Air Purifying Respirators (PAPRs), but the effective use of such equipment is vulnerable to supply shortages and inconsistently enforced usage protocols.

Medical providers may be reluctant to treat COVID-19 patients in need of time-critical diagnostic or therapeutic bronchoscopy—an essential pulmonary procedure that is seldom performed unless highly indicated in a pandemic scenario. Mitigation of exposure to pathogens associated with the pandemic is crucial to healthcare infection prevention and control. However, existing ventilatory devices and airway management systems do not provide for preventing the inadvertent release of respiratory viral droplets and aerosolized particles expelled from patient airways. When treating persons with known or suspected COVID-19, providers should don full contact and airborne personal protective equipment (PPE), including a fit-tested N95 respirator mask, a powered air purifying respirator (PAPR), and an isolation suit. However, the supply of PPE may be limited, in particular as COVID-19 infections surge in the course of the pandemic. Mechanisms for creating a closed airway system during critical care and airway management can be life-saving and have a profound effect on public health during a pandemic.

There exists a critical need to improve available technologies for effective, versatile, and low-risk modalities of ventilation in critically ill COVID patients.

BRIEF DESCRIPTION OF THE DISCLOSURE

In one aspect, a sealed access endotracheal tube adapter configured to attach to an endotracheal tube is disclosed. The adapter includes an access port that includes a first tube ending in a proximal entry port and a distal endotracheal tube connector. The proximal entry port is configured to receive at least one medical instrument and the distal endotracheal tube connector is configured to couple to a proximal end of the endotracheal tube. The adapter also includes a selectively pressurized balloon-valve seal positioned within an inner surface of the first tube distal to the proximal entry port. The balloon-valve seal includes at least two balloons attached to at least a portion of the inner surface of the first tube. The balloon-valve seal assumes a sealed configuration when the at least two balloons are inflated and the balloon-valve seal assumes an open configuration when the at least two balloons are deflated. The adapter also includes a ventilation system connector that includes a second tube with a distal end operatively coupled to the first tube between the balloon-valve seal and the distal endotracheal tube connector and a proximal end ending in a ventilation system connector. The ventilation system connector is configured to couple to a ventilation device. In some aspects, the at least one medical instrument is selected from a bronchoscope and a laryngoscope. In some aspects, each balloon of the at least two balloons includes an elastic membrane, wherein the elastic membrane and an underlying portion of the inner surface of the first tube define an inflatable volume. In some aspects, the elastic membrane includes an elastic polymer selected from latex, silicone, and rubber. In some aspects, the each elastic membrane of each balloon further includes a low-friction outer surface. In some aspects, the low-friction outer surface includes a hydrophilic coating. In some aspects, the adapter further includes an inflation port operatively connected to each inflatable volume of each balloon. The inflation port is configured to transfer a fluid into each inflatable volume to inflate and seal the balloon-valve seal and to transfer the fluid out of each inflatable volume to deflate and open the balloon-valve seal. In some aspects, the fluid is selected from air and saline solution. In some aspects, the adapter further includes a rubberized diaphragm seal positioned over the proximal entry port of the first tube. In some aspects, the adapter further includes a layer of a filtration material positioned within the first tube proximal to the balloon-valve seal positioned over the proximal entry port of the first tube.

In another aspect, an intubation mask system with a mask, at least one balloon-valve seal, a scaffold, and a plurality of removable head straps is disclosed. The mask includes at least one central opening, the least one central openings defining at least one adjacent, noncontiguous port, wherein each of the ports is configured to receive at least one medical instrument. Each balloon-valve seal is positioned within each of the at least one ports and each balloon-valve seal includes at least two balloons, wherein the balloon-valve seal assumes a sealed configuration when the at least two balloons are inflated and the balloon-valve seal assumes an open configuration when the at least two balloons are deflated. Each head strap includes a first end attached to the mask and a second end attached to the scaffold. The mask, the scaffold, and the plurality of straps are configured to secure to a head of a patient with the mask positioned on the patient's face and the scaffold positioned behind the head of the patient. In some aspects, the at least one medical instrument is selected from a bronchoscope, a laryngoscope, an endotracheal tube, a laryngeal mask airway, an orogastric tube, and a nasogastric tube. In some aspects, the mask and scaffold are formed from at least one stiff biocompatible material selected from PLA, ABS, copper composite HTPLA, and any combination thereof. In some aspects, the mask further includes a mask perimeter and a peripheral seal lining the mask perimeter, wherein the peripheral seal is configured to seal to the patient's face and to prevent pressure-induced skin injuries. In some aspects, the peripheral seal is formed using a biocompatible sealant selected from polypropylene, latex, silicon, and any combination thereof. In some aspects, the mask further includes a clear plastic sheet attached to the mask perimeter, the mask perimeter further comprising a nose bridge and a mask frame containing an internal adjustable wire, wherein the at least one central opening is contained within the clear plastic sheet and the at least one medical instrument comprises a laryngeal mask airway. In some aspects, each balloon of the at least two balloons includes an elastic membrane formed using an elastic polymer selected from latex, silicone, and rubber. In some aspects, each elastic membrane further includes a low-friction hydrophilic coating over the membrane's outer surface.

In another aspect, a quick-seal laryngeal mask airway-specific system is disclosed. The system includes a patient-fitted mask frame, a selectively inflatable cushion coupled to a proximal surface of the mask frame, a collapsible insertion channel with a mask fitting and inlet port, and a balloon-valve seal positioned within the inlet port. The mask frame defines a central opening. The cushion is configured to seal against a patient's face. The collapsible insertion channel includes a flexible tubular membrane with a proximal end and a distal end. A mask fitting is coupled to the proximal end of the flexible tubular membrane, and an inlet port is attached to the distal end of the flexible tubular membrane.

The mask fitting is further coupled to a distal surface of the mask frame over the central opening. The inlet port is configured to receive at least one of a laryngoscope and at least a portion of a laryngeal mask airway device. The insertion channel is configured to assume an extended configuration wherein the flexible tubular membrane is extended distally between the inlet port and the mask fitting and the insertion channel is further configured to assume a collapsed configuration wherein the inlet port is reversibly coupled to the mask fitting with the flexible tubular membrane stowed therebetween. The balloon-valve seal includes at least two balloons having a low-friction surface, wherein the balloon-valve seal assumes a sealed configuration when the at least two balloons are inflated and the balloon-valve seal assumes an open configuration when the at least two balloons are deflated. In some aspects, each balloon of the at least two balloons includes an elastic membrane formed from an elastic polymer selected from latex, silicone, and rubber. In some aspects, the elastic membrane further includes a low-friction hydrophilic coating.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

Figure 1A:
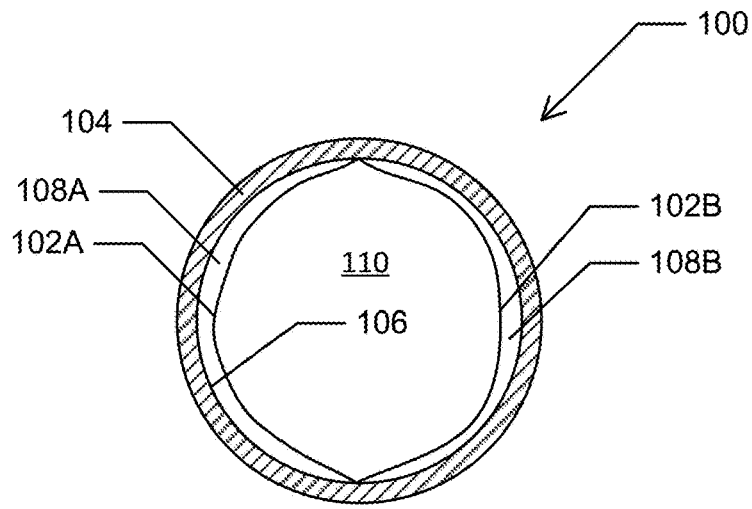
FIG. 1A is a schematic diagram of a selectively pressurized balloon-valve seal in an open configuration.

There are shown in the drawings arrangements that are presently discussed, it being understood, however, that the present embodiments are not limited to the precise arrangements and are instrumentalities shown. While multiple embodiments are disclosed, still other embodiments of the present disclosure will become apparent to those skilled in the art from the following detailed description, which shows and describes illustrative aspects of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

In various aspects, systems and devices to facilitate airway management and to reduce the risk of inadvertent release of droplets and aerosolized pathogens from the lungs of a patient are disclosed herein. The disclosed systems and devices include a balloon-valve seal that selectively opens to receive at least one medical instrument associated with an airway management procedure or treatment, including, but not limited to, a bronchoscope, a laryngoscope, or a laryngeal mask airway (LMA). In addition, the balloon-valve seal selectively closes to form an airtight seal around the at least one medical instrument. Further, the exposed surface of the balloon-valve seal may include a low-friction coating to provide for manipulation, insertion, and removal of the medical instrument without breaking the airtight seal formed by the closed balloon-valve seal. In other aspects, the balloon-valve seal may be selectively closed to form an airtight seal in the absence of the at least one medical instrument.

Figure 1B:
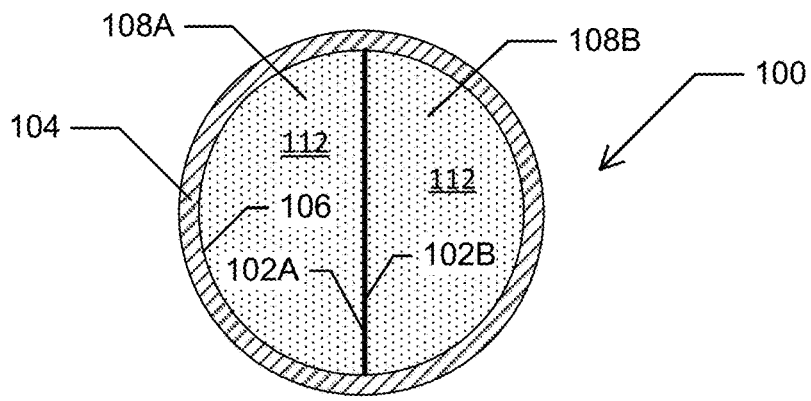
FIG. 1B is a schematic diagram of the balloon-valve seal of FIG. 1A in a sealed configuration.
Figure 1C:
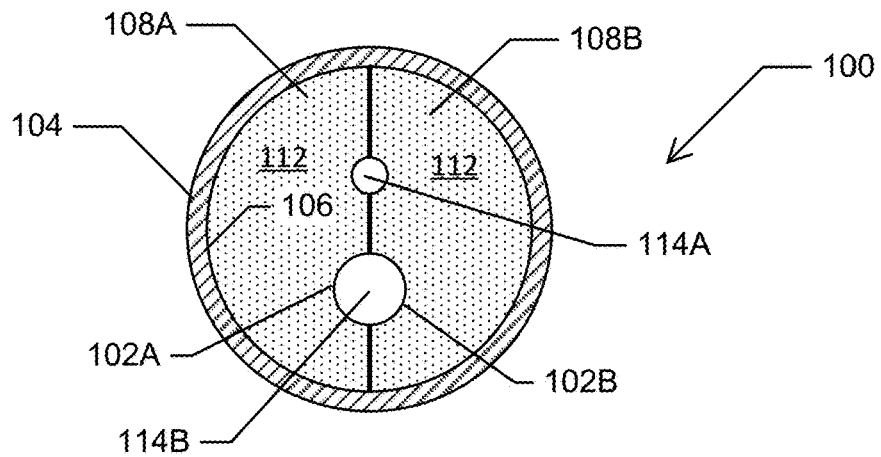
FIG. 1C is a schematic diagram of the balloon-valve seal FIG. 1A in a sealed configuration with at least one medical instrument positioned within the seal.

The principle of operation of a balloon-valve seal in one aspect is illustrated schematically in FIGS. 1A, 1B, and 1C. In the open configuration, shown illustrated in FIG. 1A, the balloon-valve seal 100 includes at least one elastic membrane 102A and 102B positioned within a surrounding wall 104. In various aspects, an inner surface 106 of the surrounding wall 104 and the at least one elastic membrane 102A and 102B form at least one inflatable volume 108A and 108B. In the open configuration, the at least one elastic membrane 102A and 102B are retracted toward the surrounding wall 104 and define a lumen that provides access through the balloon-valve seal 100.

Referring to FIG. 1B, when a fluid 112 is introduced into the at least one inflatable volume 108A and 108B, the at least one elastic membrane 102A and 102B move away from the surrounding wall 104 into the lumen 110 until the at least one elastic membrane and fluid 112 fill the lumen volume in a sealed configuration. As illustrated in FIG. 1C, one or more medical instruments 114A and 114B may be inserted through the balloon-valve seal 100 to perform an airway management procedure or treatment. In various aspects, the outer surfaces 116A and 116B of the at least one elastic membrane 102A and 102B may include a low-friction material or surface treatment to facilitate insertion or manipulation of the one or more medical instruments through the balloon-valve seal 100 while maintaining the sealed configuration to prevent the release of droplets or aerosolized pathogens from the lungs or airway of the patient.

Figure 4A:
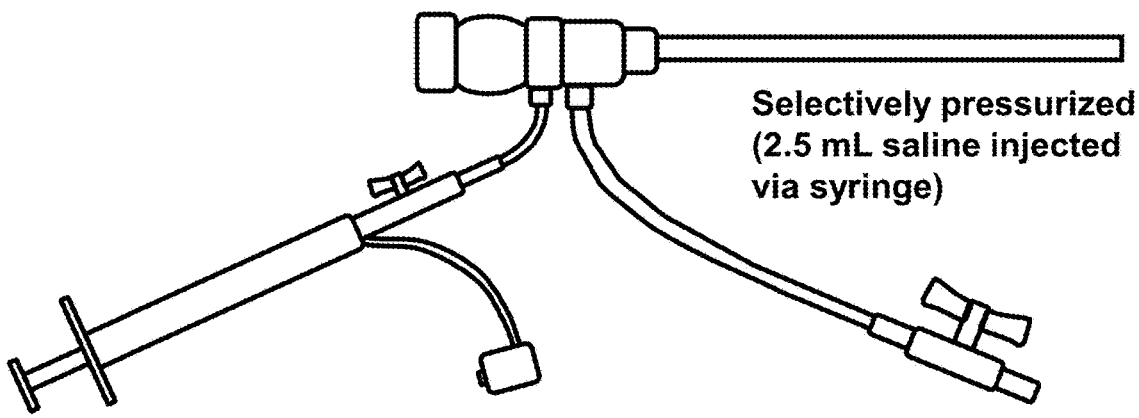
FIG. 4A is an image of a syringe of saline solution coupled to a balloon-valve seal of bronchoscope adapter in accordance with one aspect of the disclosure.
Figure 4B:
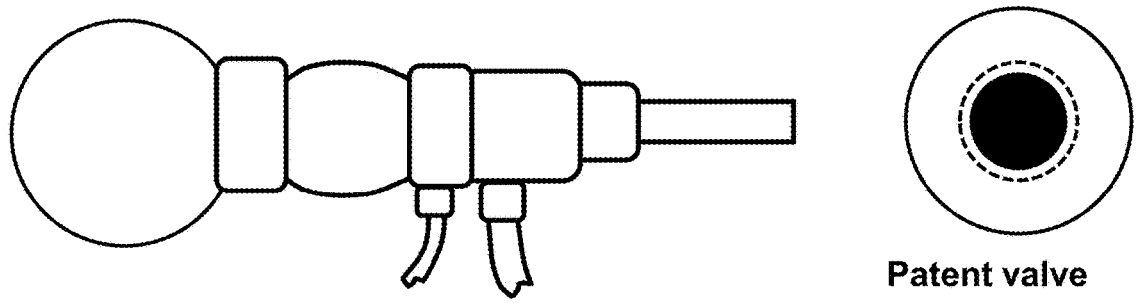
FIG. 4B is an image of the bronchoscope adapter of FIG. 4A showing the balloon-valve seal (inset image) in an open position.
Figure 4C:
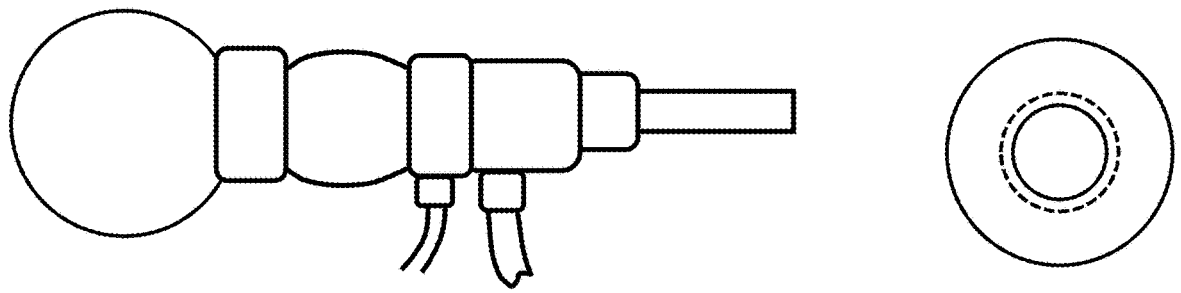
FIG. 4C is an image of the bronchoscope adapter of FIG. 4A showing the balloon-valve seal (inset image) in a closed position.

In various aspects, the balloon-valve seal includes any suitable number of elastic membranes without limitation. In one aspect, the balloon valve seal includes one elastic membrane, as illustrated in FIG. 4B and FIG. 4C. In another aspect, the balloon valve seal includes two elastic membranes defining two balloons within the surrounding wall of the valve seal. In various other aspects, the balloon valve seal includes three elastic membranes, four elastic membranes, five elastic membranes, six elastic membranes, seven elastic membranes, eight elastic membranes, nine elastic membranes, ten elastic membranes, or more.

Any suitable elastic material may be used to form the elastic membranes without limitation. In various aspects, the material of the elastic membrane may be any suitable elastic material capable of forming a thin deformable film with sufficient strength and/or toughness to resist damage during use as described below. Non-limiting examples of suitable elastic materials include elastic polymers such as latex, silicone, and rubber. In some aspects, the material of the elastic material may be further provided with a low-friction surface using any suitable means including, but not limited to, selection of a low-friction material and functionalization or coating of the membrane surface to reduce surface friction. By way of non-limiting example, the elastic membrane may be provided with a hydrophilic surface coating to reduce the surface friction of the membrane.

In various additional aspects, the balloon-valve seal is provided with a fluid source operatively coupled to introduce a fluid into the at least one inflatable volume. The introduced fluid may be any suitable fluid without limitation including, but not limited to, a gas such as air or nitrogen, and a liquid such as water or saline solution. In various aspects, the fluid source includes a means of introducing the fluid into the at least one inflatable volume including, but not limited to, a pump and a syringe. In various other aspects, the balloon-valve seal is provided with a means of removing the fluid from the at least one inflatable volume including, but not limited to, a pump, a syringe, and/or a pressure relief valve. In some aspects, the means of introducing and removing the fluid to/from the at least one inflatable volume may be the same device including, but not limited to, a syringe and/or a pump with a pressure relief valve.

In use, the amount of fluid introduced or removed from the at least one inflatable volume may be modulated to fine-tune the rigidity, sliding friction, seal effectiveness, and any other relevant parameter characterizing the seal formed by the balloon-valve seal during any stage of an airway management or airway treatment procedure. By way of non-limiting example, a small amount of fluid may be removed from a balloon seal valve in the sealed configuration to reduce the sliding friction associated with fine-tuning the placement of a medical instrument through the balloon-valve seal, while maintaining an airtight seal.

The inclusion of one or more balloon-valve seals in the devices and systems described herein overcome at least a portion of the shortcomings of several existing airway management devices and systems. Some existing airway management devices include passive locking of medical instruments such as bronchoscopes to airway management devices, but typically do not provide a continuous airtight seal to the external environment while inserting, manipulating, and/or removing the medical instrument from the airway management device. Other existing airway management devices include rigid adjustable seals that provide an airtight seal to the external environment, but lack sufficient flexibility for precise device manipulation and/or accommodation of a variety of medical instrument sizes. In various aspects, described below, the at least two selectively pressurized, low friction balloons of the balloon-valve seal act as a valve between patient airways and the environment. The selectively pressurized balloon-valve seal provides an airtight seal that may be adjusted or regulated to maintain an adequate seal while avoiding excessive or rigid pressures that may limit procedural dexterity and device manipulation.

In various aspects, described below, the selectively pressurized balloon-valve seal described above is incorporated into a variety of airway management systems and devices including, but not limited to, bronchoscope adapters, endotracheal tubes (ETTs), patient masks to facilitate containment of droplets and aerosolized pathogens during endotracheal intubation and subsequent airway treatment, and patient masks to facilitate containment of droplets and aerosolized pathogens during placement and use of laryngeal mask airway devices and subsequent airway treatment.

I. Bronchoscope Adapter

In various aspects, an endotracheal tube adapter designed to provide a reliable, modifiable, non-rigid seal for the prevention of aerosolized particle spreading during bronchoscopy is disclosed. An endotracheal tube adapter 200 in one aspect is shown illustrated in FIG. 2. The adapter 200 includes an access port 202 ending in a proximal entry port 204 and a distal endotracheal tube connector 206. The adapter further includes two hydrophilically coated, low-friction balloons 208 positioned along the interior surface of the access port wall 210 to form a selectively pressurized balloon-valve seal 100A. The endotracheal tube adapter 200 further includes a ventilation inlet 212 with a ventilation system connector 214 at a proximal end and connecting into the access port 202 at a distal end.

Figure 6:
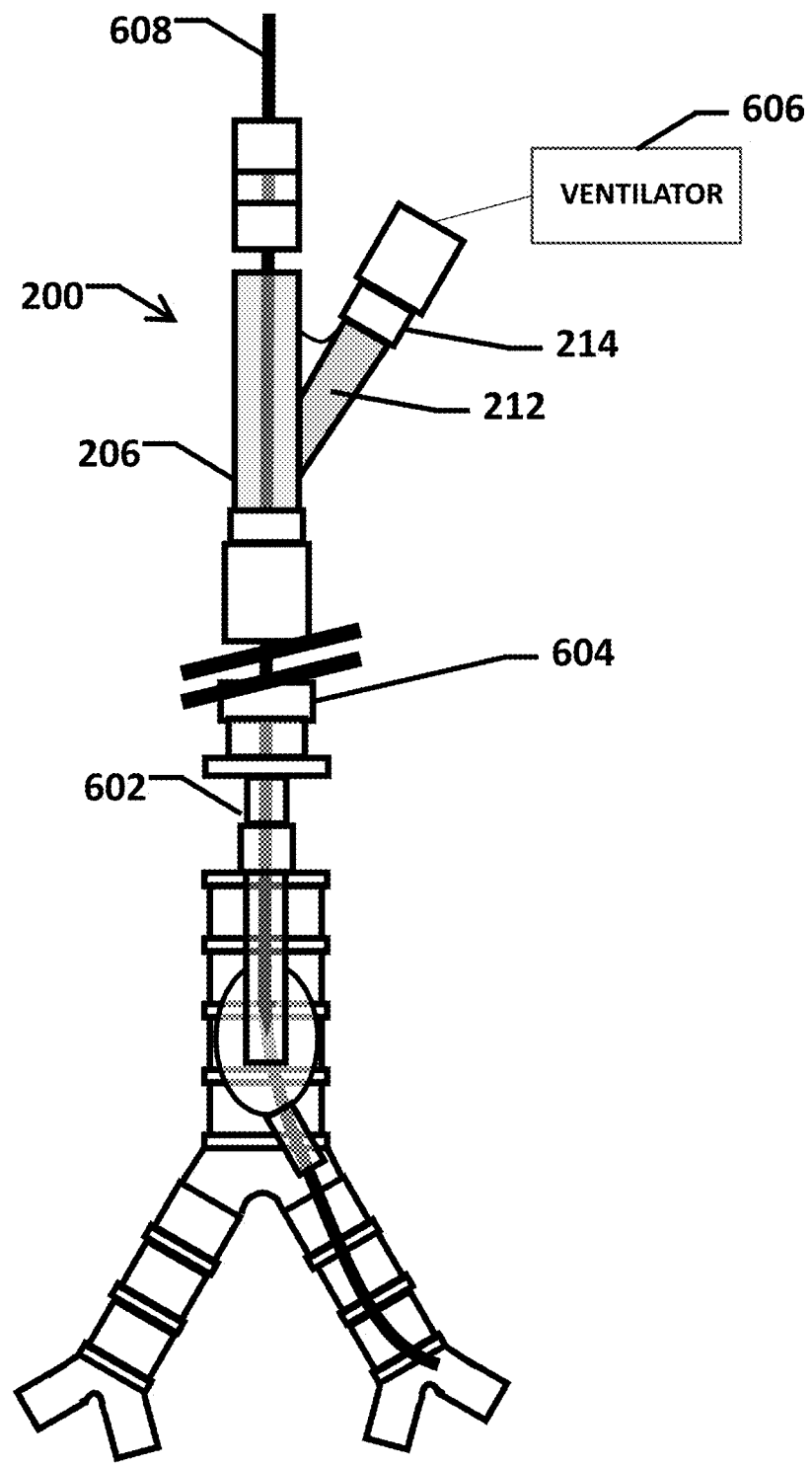
FIG. 6 is an image of an airway management system that includes a single-lumen endotracheal tube coupled to a bronchoscope sealable access port adapter with a sealable access port in accordance with one aspect of the disclosure.

As illustrated in FIG. 6, the endotracheal tube adapter 200 is configured to couple to a proximal end 604 of an endotracheal tube 602 at the distal endotracheal tube connector 206 to facilitate access to the endotracheal tube by one or more medical instruments associated with an airway maintenance procedure or treatment. In addition, the ventilator inlet 212 of the endotracheal tube adapter 200 is configured to couple to a ventilator 606 (not illustrated) at the ventilation system connector 214 in a sealed connection. In some aspects, the ventilation system connector 214 may be coupled to a HEPA filter and/or sputum trap to capture particulates flowing out via relative negative pressure+/− suction catheter for selective application of additional negative pressure during an airway maintenance or treatment procedure. In various aspects, the balloon-valve seal 100A and sealed connection at the ventilation system connector 214 together form airtight seals that prevent the release of droplets and aerosolized pathogens from the lungs of an intubated patient during ventilation or during airway procedures using medical instruments such as a bronchoscope 608, as illustrated in FIG. 6.

Referring again to FIG. 2, when the endotracheal tube adapter 200 is positioned for bronchoscope procedures, the balloons 208 are inflated by the introduction of a fluid as described above to create an airtight but non-rigid seal. In some aspects, the adaptor 200 may be provided with an inflation port 216 to transfer fluid into and/or out of the balloons 208 to configure the balloon-valve seal into an open (see FIG. 4B) or sealed (see FIG. 4C) position. Any suitable systems or devices for transferring fluid may be selected for use as the inflation port 216 without limitation. In some aspects, the inflation port may include a hand pump and a valve to pump air into the balloons 208 and to vent air from the balloons. In other aspects, the inflation port may be coupled to a syringe as illustrated in FIG. 4A to inject and withdraw saline solution to/from the balloons. In other additional aspects, the inflation port may be connected to a liquid or gas fluid source in combination with at least one pump to transfer the fluid between the fluid source and the balloons. In some aspects, the inflation port may include separate conduits for the insertion and removal of fluid to/from the balloons. By way of non-limiting example, as illustrated in FIG. 4A, the inflation port may include a syringe coupled to a feed line to pressurize a fluid (saline) within the balloons and a separate vent line provided with a valve that regulates the fluid pressure by opening and closing.

Figure 2:
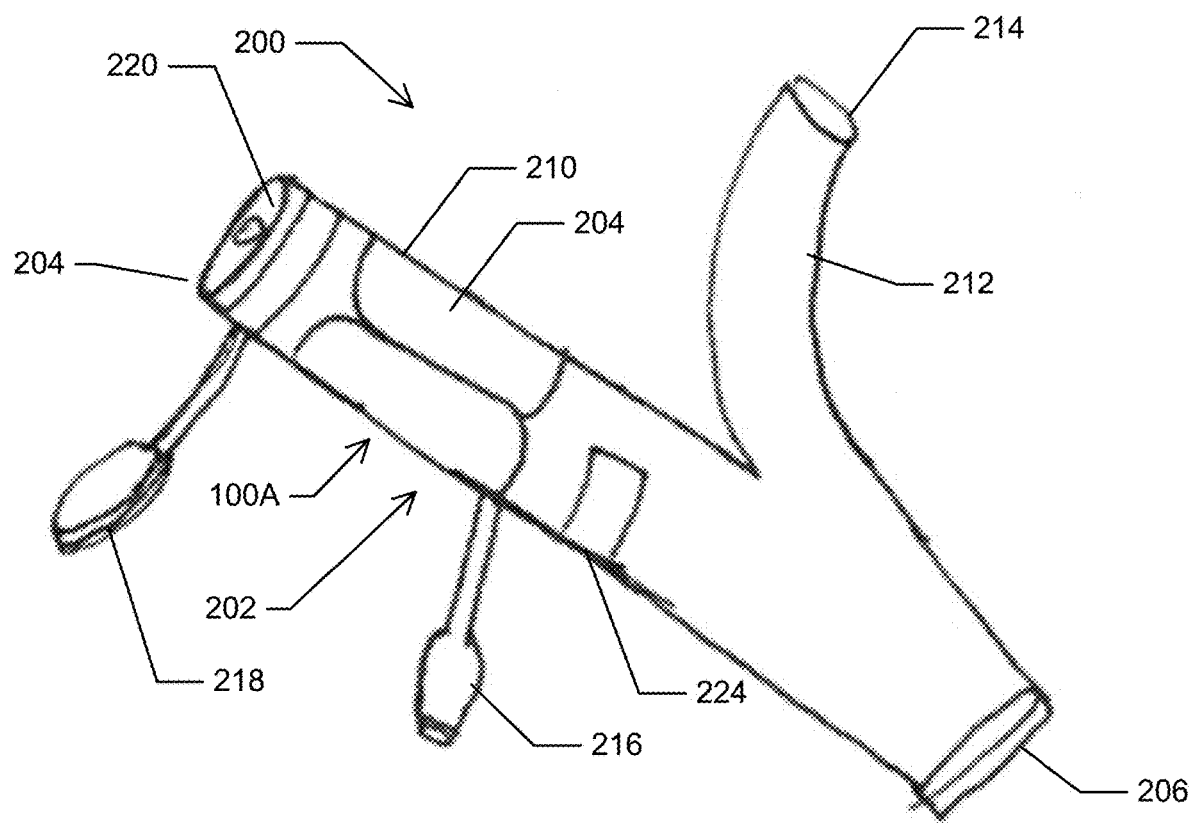
FIG. 2 is a side view of a bronchoscope adapter with a sealable access port in accordance with one aspect of the disclosure.
Figure 3:
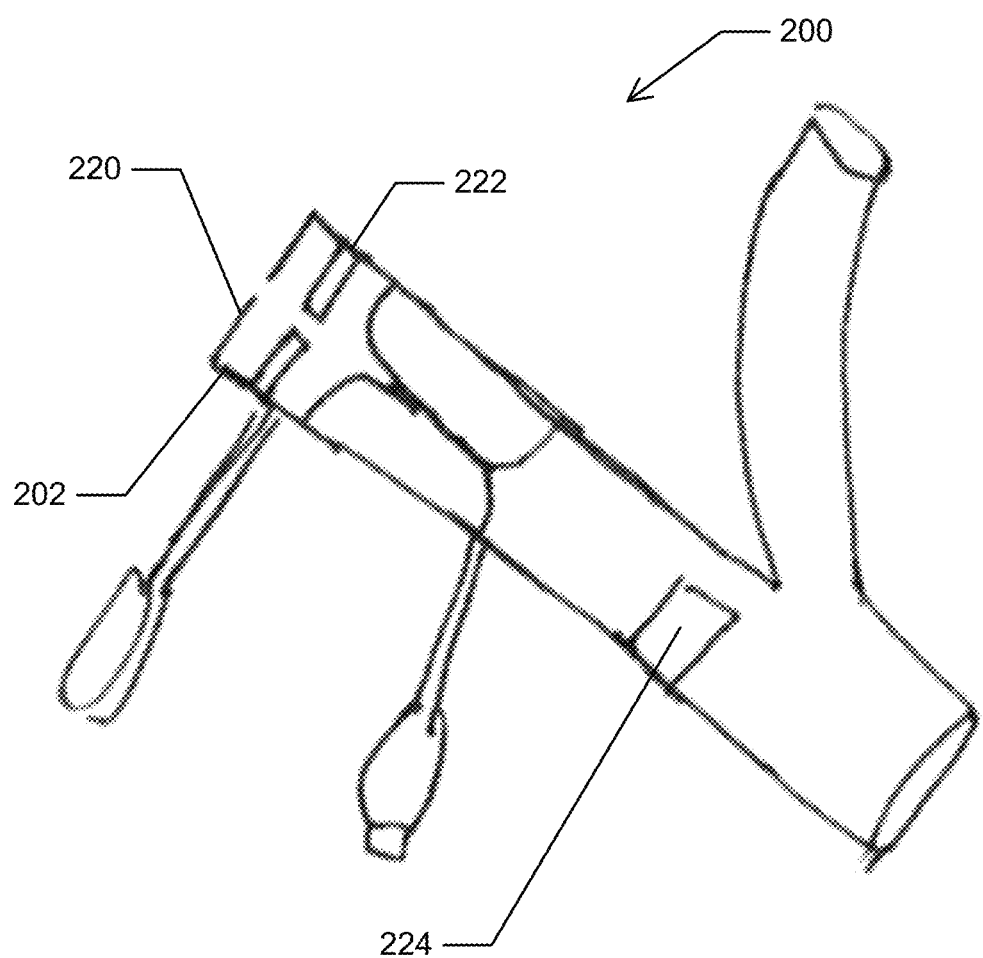
FIG. 3 is a side cutaway view of the bronchoscope adapter of FIG. 2.

Referring to FIG. 2 and FIG. 3, the adapter 200 may be provided with a rubberized diaphragm seal 220 to provide additional sealing of the access port 202 when a medical instrument is inserted and manipulated. In other additional aspects, the adapter 200 may be provided with a layer of filtration material 222 forming a ring of protection proximal to the sealed balloon valve 204 to mitigate the spread of exhaled particles from patient airways.

Bronchoscopes or other medical instruments of varying diameters can be advanced with relative ease through the low-friction balloons 208 of the adapter 200 so that procedural dexterity of the operator is maintained while also maintaining the airtight seal of the access port 202. When not in use, the balloon-valve seal 100 can be maximally inflated and capped to maintain device integrity. In some aspects, the adapter 200 may be further provided with an entry port cap 218 that seals over the entry port 204 when the entry port 204 is not in use. Any suitable sealable cap may be selected for use as the entry port cap 218 without limitation. In one aspect, illustrated in FIGS. 4B and 4C, the entry port cap may be a durable, hemisphere-shaped, resilient elastomer cap (e.g. polyurethane) with a base that fits snugly over the access port. The elastomer cap may further include a dome top with a central opening lined by inward-facing balloon cusps (i.e. analogous to cusps on heart valves) for approximating a seal around the bronchoscope.

In various additional aspects, the endotracheal tube adapter 200 may further include a sealed viral sampling access port 224 (see FIGS. 2 and 3) to accommodate real-time biosensors (not shown) used for continuous or intermittent monitoring of a patient's airways for the presence of pathogens without disconnecting the adapter 200 or ventilator. If a biosensor adapter were fixed within the airways of all suspected and known COVID-positive patients, healthcare providers would be less reluctant to perform the dangerous task of disconnecting a ventilator circuit to add in a bronchoscope adapter. This event not only exposes healthcare workers to aerosolized particles but also increases the risk of alveolar decruitment in patients with acute respiratory distress syndrome.

By way of non-limiting example, the adapter comprises an outer silicone tube and an inner film tube with an attached stopcock for pressurizing the valve. Saline or air is injected through the attached stopcock to create an airtight but non-rigid seal, which limits the dispersion of aerosolized particles and simultaneously allows the operator to advance scopes of varying diameters. This system is adaptable to many procedures requiring patient airway access, including bronchoscopy and nebulizer treatment. An airtight seal at the bronchoscope access port can be achieved in real-time via the injection of fluid through an inflation port. This balloon-valve system is easily operable, accommodates scopes of varying diameters, and maintains a reliable seal during procedural manipulation.

II. Endotracheal Tube

Figure 5:
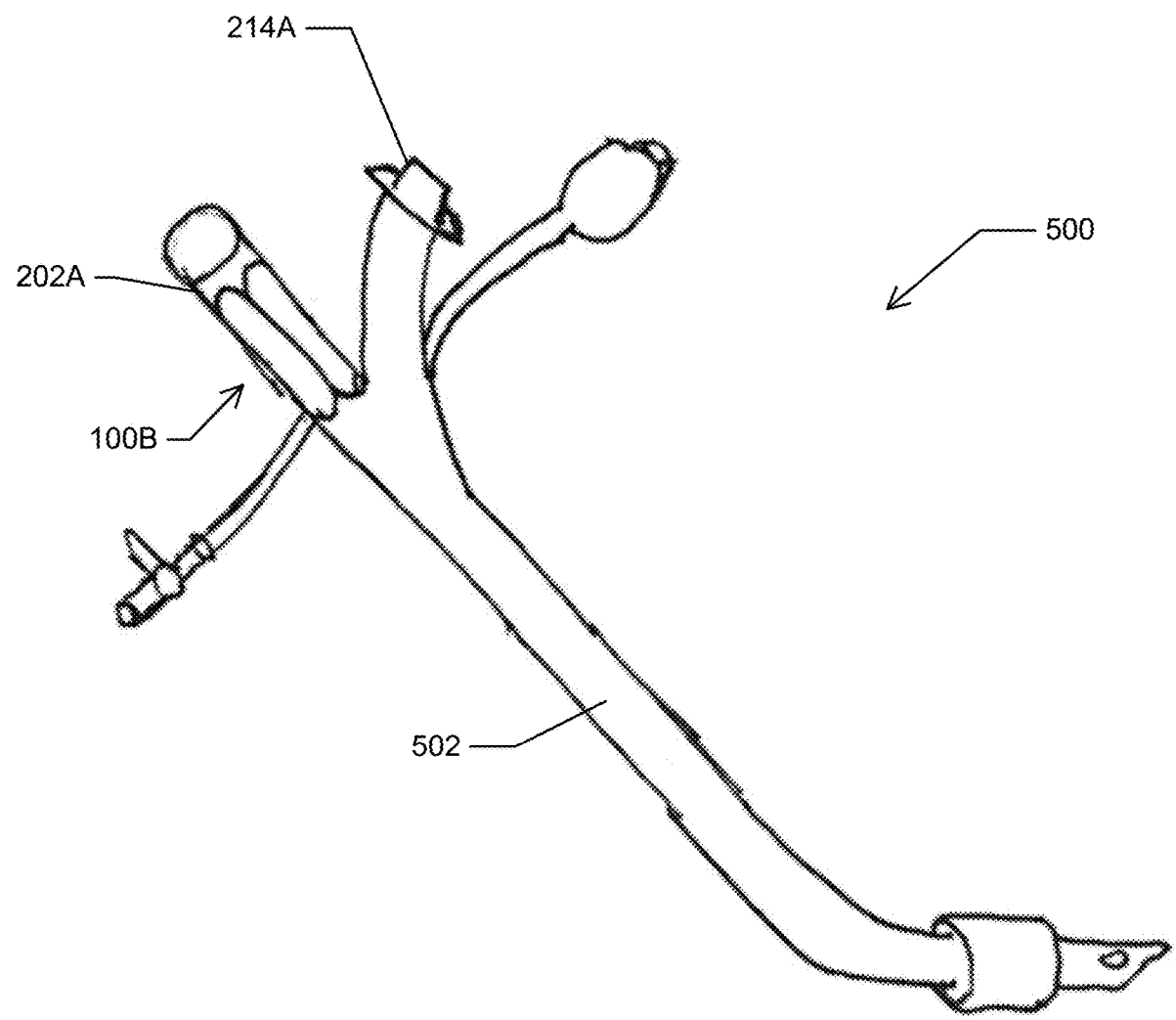
FIG. 5 is a side view of an endotracheal tube with a sealable bronchoscope access port in accordance with one aspect of the disclosure.

In various aspects, the endotracheal tube adapter 200 may be combined with the features of an existing endotracheal tube to form an integral sealed multiport endotracheal tube (ETT). As illustrated in FIG. 5, the sealed multiport endotracheal tube 500 includes a balloon-sealed bronchoscope port 202A suitable for use in COVID-positive patients requiring endotracheal intubation. This ETT 500 can be used interchangeably for a number of critical procedures commonly performed in the setting of COVID and other virulent pathogens.

In various aspects, the ETT 500 incorporates design elements similar to the endotracheal tube adapter 200 described above. In some aspects, the ETT 500 includes a standard PVC single-lumen ETT 502 with the added functionality of a bronchoscope port 202A that is continuous with the ETT tube and capable of sealing around scopes of various sizes. The proximal end of the ETT 500 into two arms that form a "Y" configuration, with each arm serving a distinct function: (1) a traditional respiratory circuit attachment point 214A, and (2) a sealable balloon-valve 100B for bronchoscope procedures.

III. Endotracheal Intubation Mask

Figure 7:
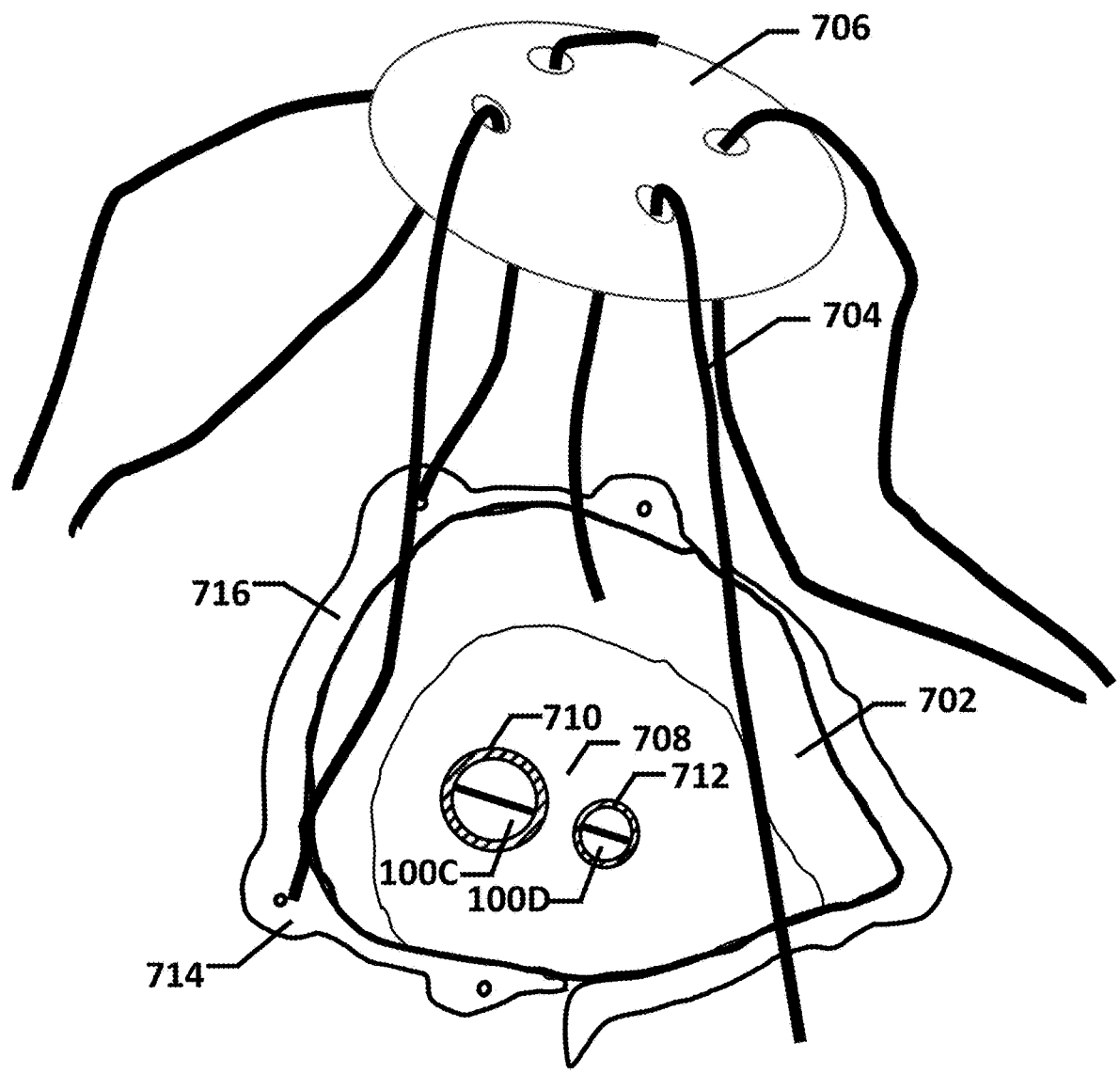
FIG. 7 is an image of a 3D printed mask with a removable scaffold designed for use with a laryngoscope, ETT, and/or oro/nasogastric tubes in accordance with one aspect of the disclosure.

In various aspects, a mask and integral scaffold with removable head strap attachments are described. FIG. 7 shows a mask system 700 in one aspect that includes a mask 702 and a plurality of removable head straps attached at opposite ends to attachments 714 formed on the anterior surface of the mask 702) to a removable scaffold 706 positioned posteriorly behind the head of a patient (not shown). In some aspects, the scaffold 706 and mask 702 can be 3D printed using any suitable stiff biocompatible material including, but not limited to, PLA, ABS, copper composite HTPLA, and any combination thereof. Any suitable material may be used in the construction of the removable head straps 704 including, but not limited to, nylon, elastic, other synthetic fibers, and any combination thereof.

Figure 8:
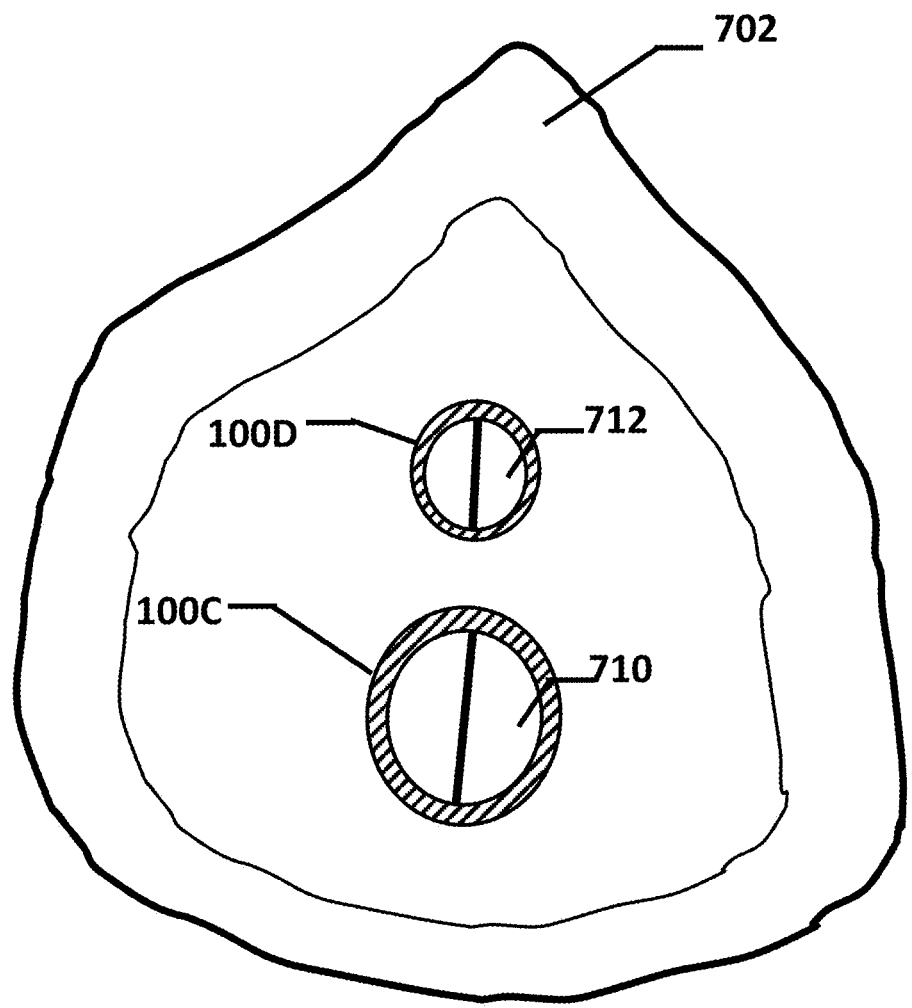
FIG. 8 is an image of an inner surface of the 3D printed mask of FIG. 7 showing the access ports for the introduction of a laryngoscope, ETT, and/or oro/nasogastric tubes to a patient.

In various additional aspects, shown illustrated in FIGS. 7 and 8, the mask system 700 further includes at least one central opening 708 provided with two adjacent, noncontiguous ports 710 and 712 through which a laryngoscope, ETT, and oro/nasogastric tubes (not shown) can be inserted. Frictionless, balloon-sealable valves 100C and 100D are positioned within ports 710 and 712, respectively, to provide reliable and adjustable seals around medical equipment during placement, adjustment, and removal as described above.

Referring again to FIG. 7, mask 702 may further include a peripheral seal 716 lining the mask perimeter to provide a comfortable fit on the patient's face (not shown) and to prevent pressure-induced skin injuries. The peripheral seal 716 may be formed using any suitable biocompatible sealant including, but not limited to, polypropylene, latex, silicon, and any combination thereof.

In various aspects, the mask system 700 is designed to inhibit the spread of aerosolized particles from a patient's oral cavity, to permit freedom of movement for inserted scopes and tubes, and to facilitate easy application and removal of the mask. For patients undergoing videoscope-guided endotracheal intubation, the two centrally located, balloon-sealable ports in the mask provide coverage for critical leaks around the tracheal balloon cuff of the endotracheal tube (ETT). In some aspects, the mask can be fitted over the patient's nose and mouth during a laryngoscope placement of an ETT to provide protection throughout the procedure as well as to provide long-term ventilation, as illustrated schematically in FIGS. 9A, 9B, 9C, 9D, 9E, and 9F.

Figure 9A:
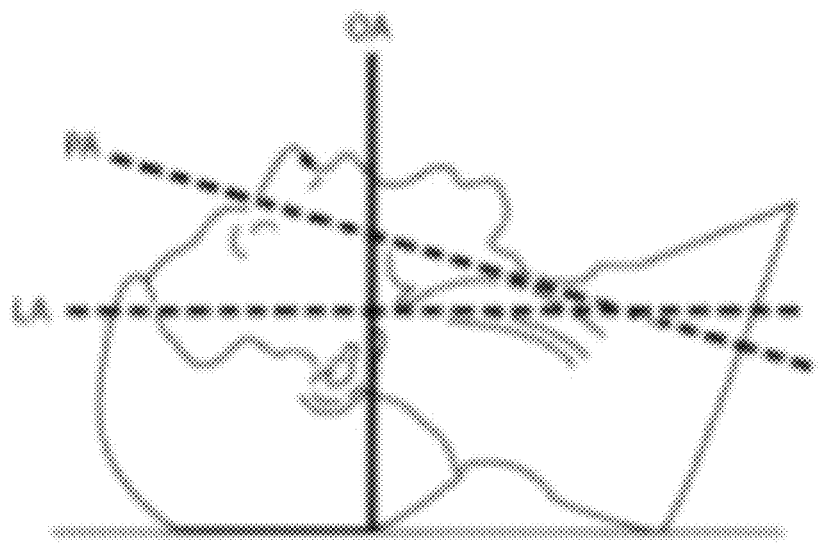
FIG. 9A is a schematic illustration of a first step in a method of laryngoscope and endotracheal tube placement in a patient using the 3D printed mask of FIG. 7 and FIG. 8 in accordance with one aspect of the disclosure, showing the patient lying supine with neck in neutral position.
Figure 9B:
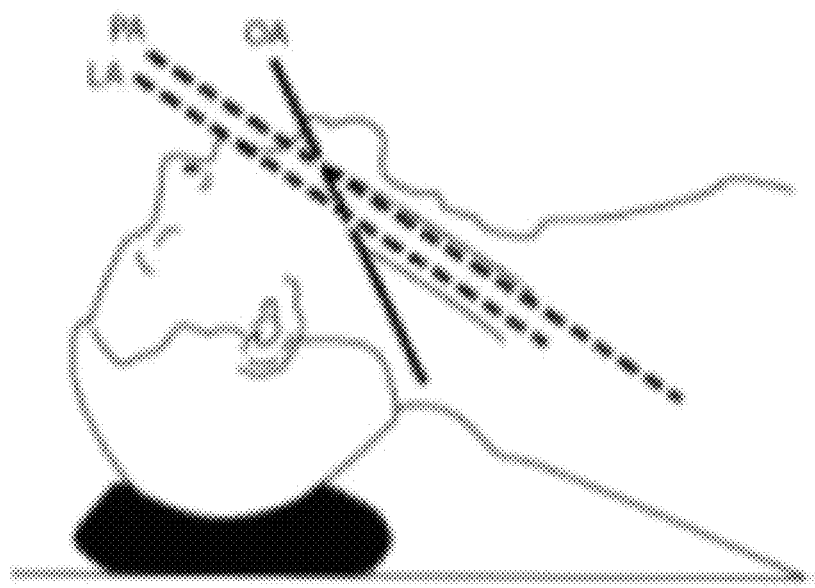
FIG. 9B is a schematic illustration of a second step of the method of FIG. 9A, illustrating extending and elevating the patient's head (for desired neck flexion) to align the pharyngeal axis (PA) and laryngeal axis (LA) for optimal laryngeal visualization.
Figure 9C:
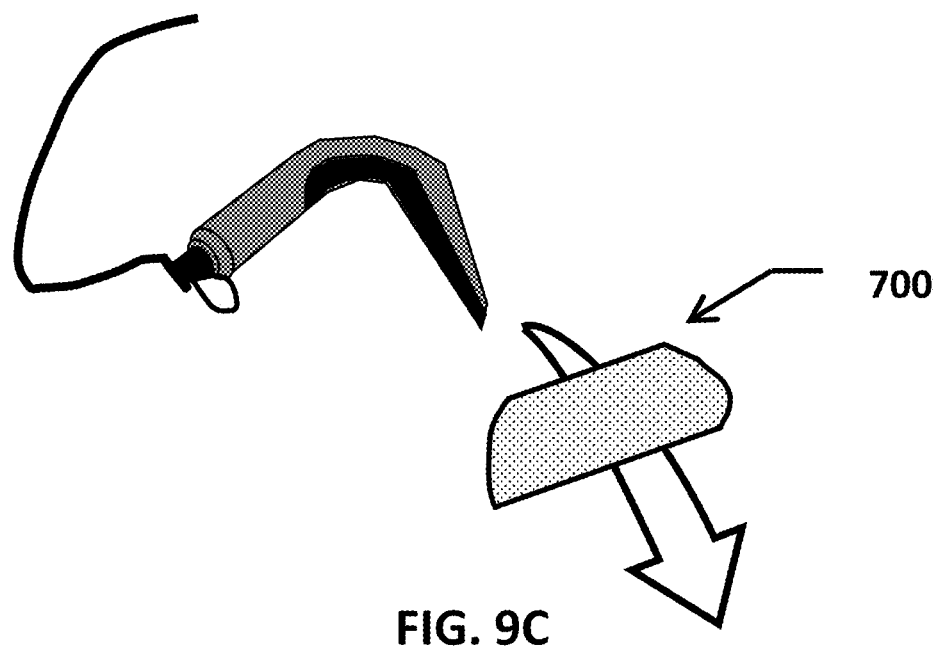
FIG. 9C is a schematic illustration of a third step of the method of FIG. 9A, showing the advancement of the laryngoscope through one of two balloon-sealable ports in a mask similar to the mask of FIG. 6 and FIG. 7.
Figure 9D:
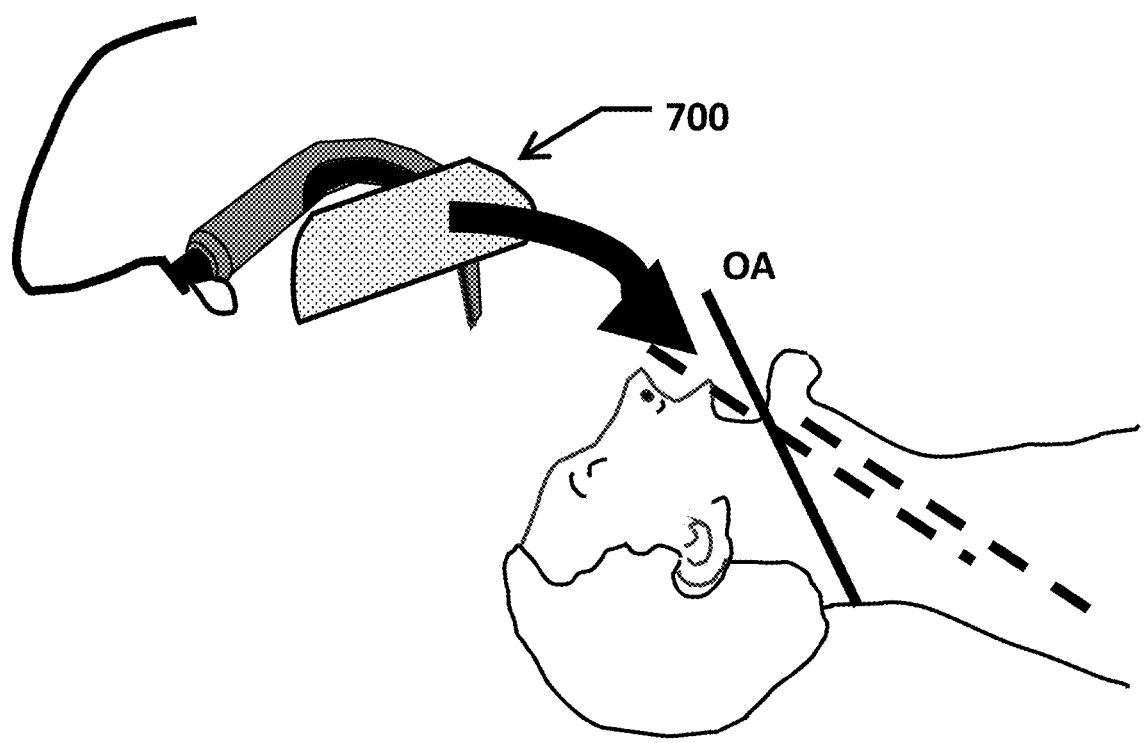
FIG. 9D is a schematic illustration of a fourth step of the method of FIG. 9A, showing the initial advancement of a distal end of the laryngoscope projecting from one sealed port of the mask toward the patient's head.
Figure 9E:
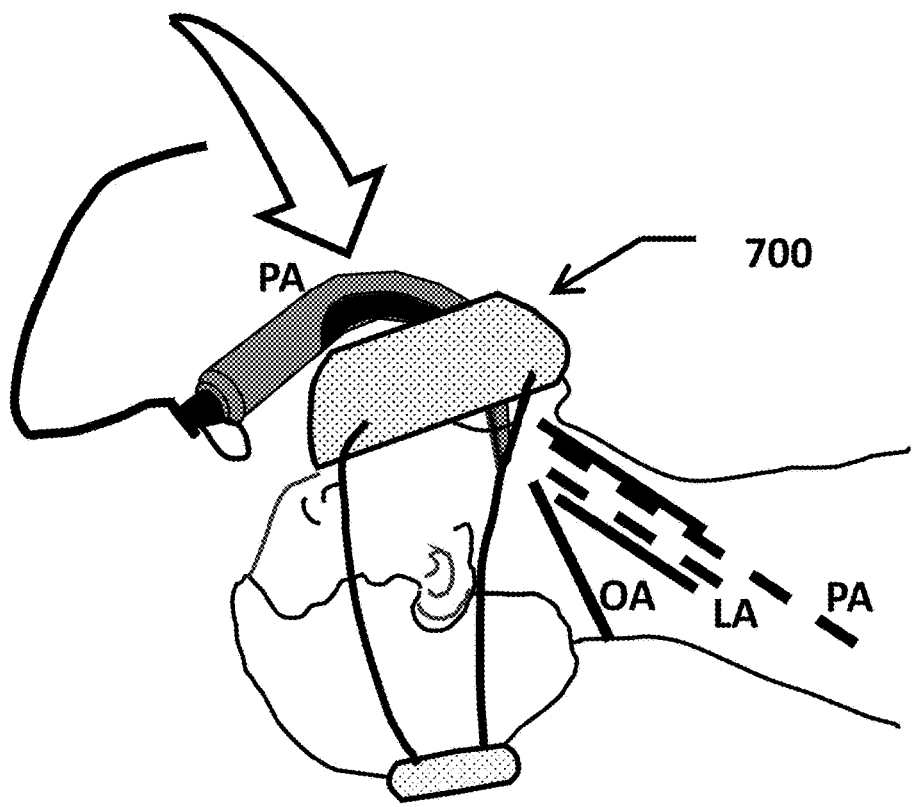
FIG. 9E is a schematic illustration of a fifth step of the method of FIG. 9A, showing the securing of the mask to the patient's head after the laryngoscope has been inserted orally into the patient.
Figure 9F:
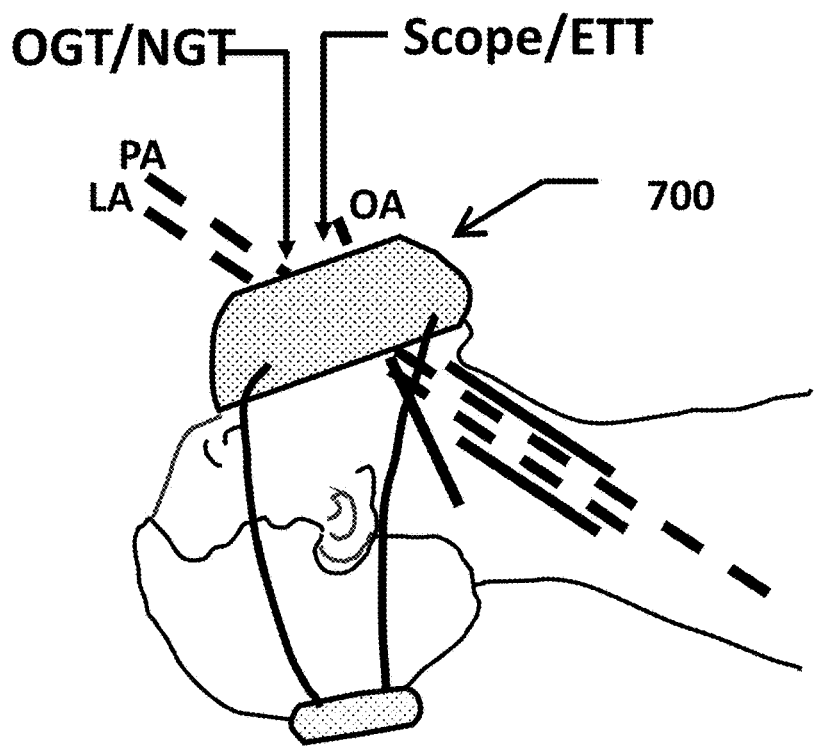
FIG. 9F is a schematic illustration of a sixth step of the method of FIG. 9A, showing the advancement of the endotracheal tube through the same balloon-sealable port as the laryngoscope into the trachea under the guidance of the laryngoscope to provide oxygenation to the patient.

FIG. 9A shows a patient lying supine with the neck in neutral position. Referring to FIG. 9B, when opening the airway, the patient's head is extended and elevated (for desired neck flexion) to align the pharyngeal axis (PA) and laryngeal axis (LA) for optimal laryngeal visualization. Referring to FIG. 9C, prior to laryngoscope (GlideScope) insertion, the laryngoscope is advanced through one of the two balloon-sealable ports in the mask. Near the distal end of the scope, the balloon-sealable port of the mask can be sealed by an operator via the selectively pressurized balloon valves, as described above. Referring to FIG. 9D, the laryngoscope is advanced towards the patient's face with the mask adapter initially providing loose coverage of airways. Referring to FIG. 9E, once the laryngoscope is inserted orally, the mask is secured around the patient's head. The laryngoscope is then fully advanced and positioned for proper laryngeal visualization on a video camera (not shown), as illustrated in FIG. 9F. The ETT is advanced through the same balloon-sealable port while maintaining the seal via adjusting the pressure in the balloon-valve system. Using the laryngoscope and video camera to guide placement, the ETT is inserted orally into the trachea to provide oxygenation. In some aspects, the second balloon-sealable port is available for oro/nasogastric tube (OGT/NGT) passage in intubated patients receiving long-term ventilation.

IV. Laryngeal Airway Mask

In various aspects, a laryngeal mask airway (LMA)-specific mask system is disclosed. The LMA-specific mask system is designed to provide broad coverage of a patient's lower face (i.e. with mouth opened or closed), to provide adequate visualization of the airways through a sheet of clear plastic (see FIG. 11), and to provide a sealed fit around the patient's face enabled by an inner adjustable wire and surrounding material forming a nose bridge and a pliable mask frame to which are attached adjustable straps around the patient's head. In patients with difficult airways for intubation or cases in which temporizing measures of ventilation are needed, the disclosed LMA-specific mask system may be used for quick, easy, and relatively safe airway access and oxygenation. The mask can be fitted over the patient's nose and mouth during LMA placement to provide protection throughout the procedure as well as during short-term ventilation.

Figure 10:
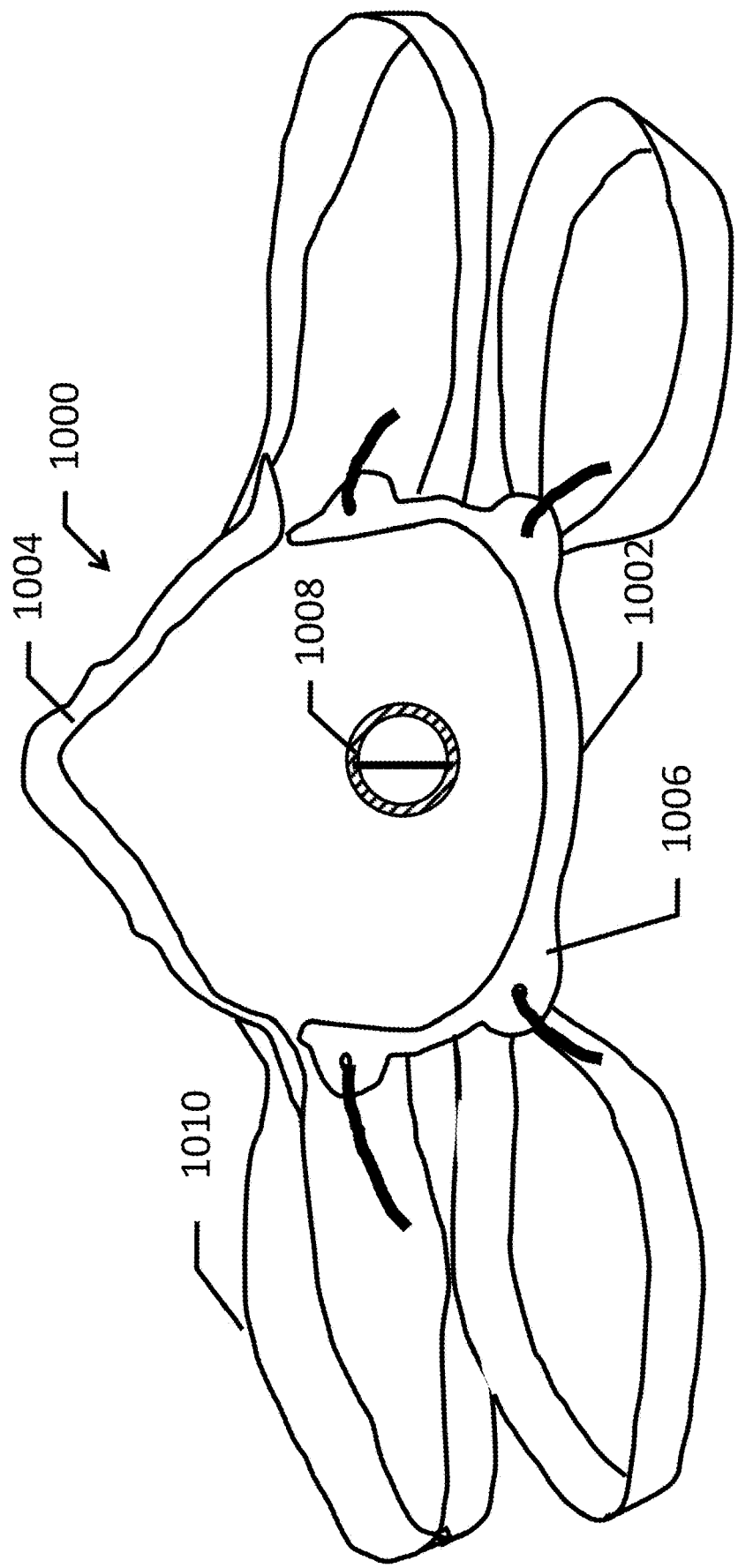
FIG. 10 is an image of a 3D printed mask with a pliable frame and transparent plastic cover designed for use with a laryngeal airway mask in accordance with one aspect of the disclosure.
Figure 11:
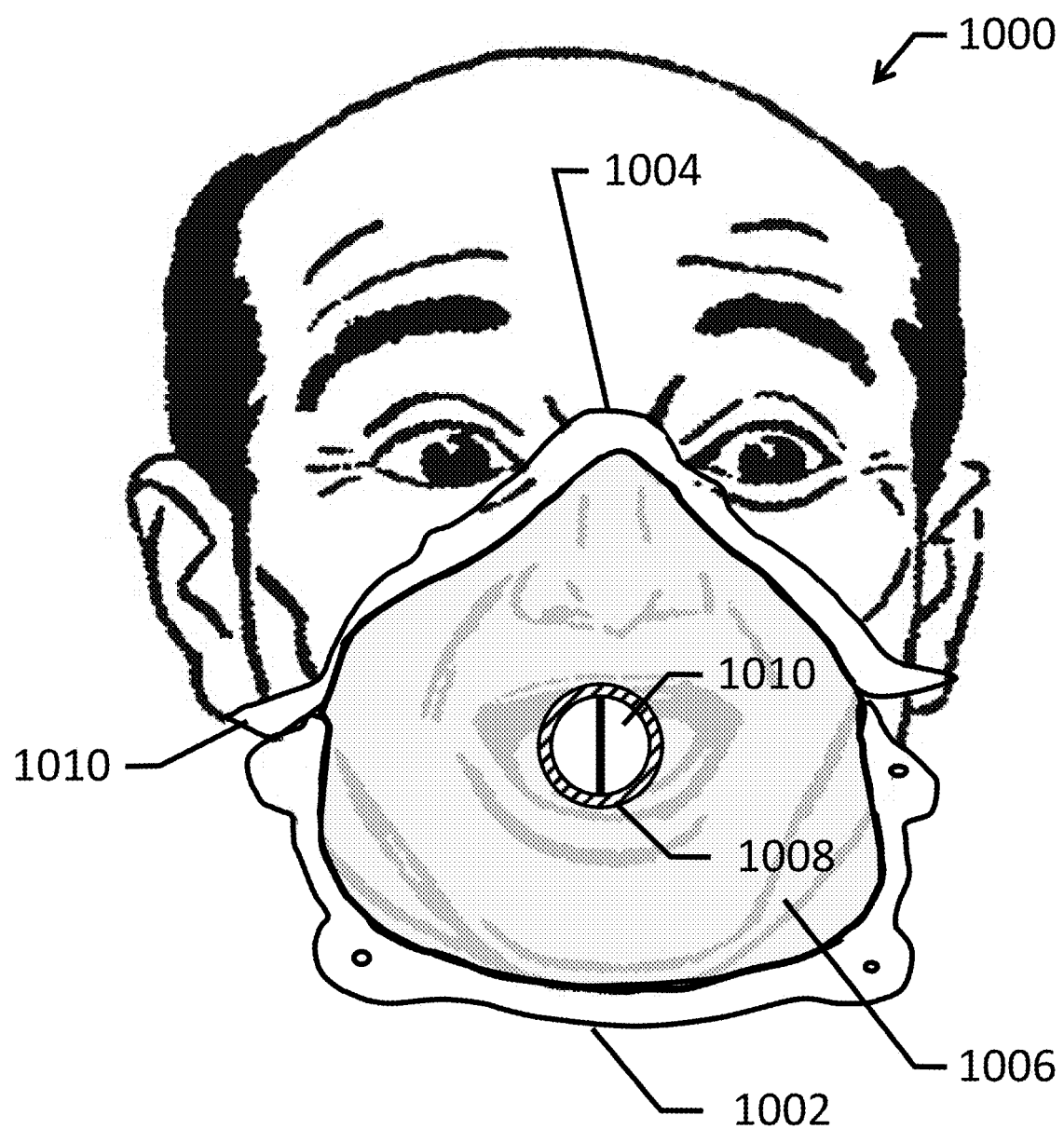
FIG. 11 is an image of the mask of FIG. 10 fitted on the head of a patient.

A laryngeal mask airway (LMA)-specific mask system 1000 in one aspect is illustrated in FIGS. 10 and 11. The mask system 1000 includes a pliable mask frame 1002 and wire-reinforced nose bridge 1004 supporting a flexible sheet cover 1006 that includes a central access port 1008 sealed within the sheet cover 1006. The mask frame 1002 may be constructed of any suitably stiff biocompatible material including PLA, ABS, and any combination thereof. The mask cover 1006 is constructed of any suitable biocompatible material with low stiffness and relatively transparent properties including, but not limited to, FEP, PETG, and any combination thereof. In various aspects, the mask frame 1002 and wire-reinforced nose bridge 1004 are configured to accommodate both open and closed mouths. In various other aspects, the sheet cover 1006 may be provided with different sizes/shapes of plastic cover to similarly accommodate both open and closed mouths of patients as may occur during the placement of an LMA.

In some aspects, at least a portion of the mask system 1000 may be fabricated using 3D printing devices and methods. The pliable mask frame 1002 and wire-reinforced nose bridge 1004 may be 3D printed as two thin and attachable frame elements. The flexible sheet cover 1006 may be 3D printed in the form of a sheet.

The system central port 1008 contains a frictionless, balloon-sealable valve 1010 (described above) through which an LMA can be inserted. The valve 1010 provides a reliable seal during placement, adjustment, and removal of an LMA in a patient. In some aspects, the mask frame 1002 and wire-reinforced nose bridge 1004 are lined with a biocompatible sealant (not illustrated) including, but not limited to polypropylene, latex, silicon, and any combination thereof. The sealant provides a comfortable fit on the patient's face and prevents pressure-induced skin injury.

Referring again to FIGS. 10 and 11, the mask system 1000 further includes a plurality of removable head straps 1010 attached to the frame 1002 and nose bridge 1004. The removable head straps 1010 may be constructed of any suitable material including, but not limited to, nylon, elastic, other synthetic fibers, and any combination thereof. In some aspects, the head straps 1010 may be configured to secure the mask frame 1002 at four points and across the nose bridge 1004.

FIG. 11 illustrates at least several useful properties of the LMA-specific mask system. The mask frame is pliable and may be held in place with straps secured tightly around the head of the patient. In some aspects, four points held in place by electric wire may serve as attachment points for head straps to hold the pliable frame in the desired conformation. In addition, the mask design provides the ability to remain sealed to the patient's face for a full range of mouth positions ranging from fully open to fully closed.

Figure 12A:
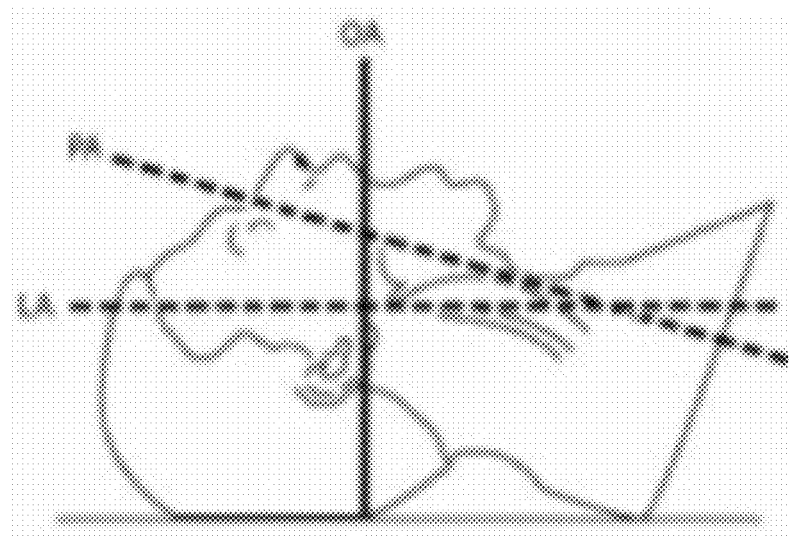
FIG. 12A is a schematic illustration of a first step in a method of laryngeal airway mask placement in a patient using the 3D printed mask of FIG. 10 and FIG. 11 in accordance with one aspect of the disclosure, showing the patient lying supine with neck in neutral position.
Figure 12B:
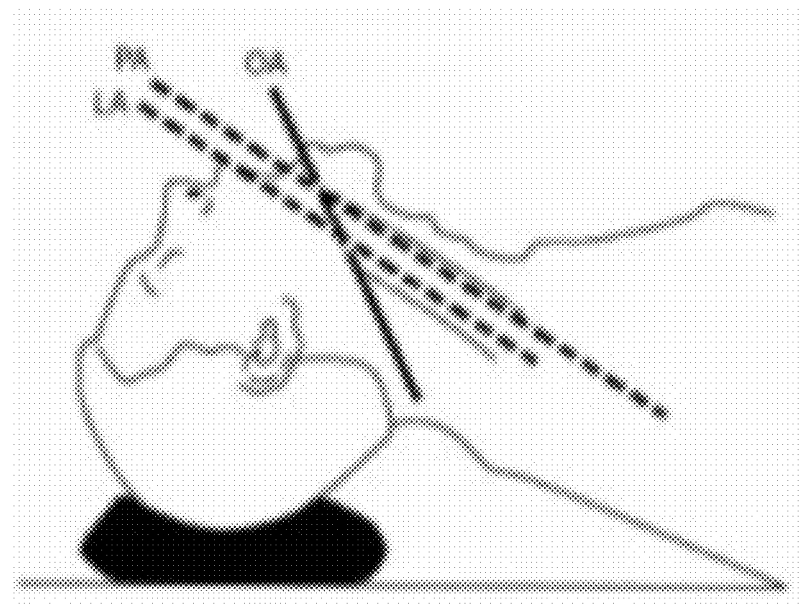
FIG. 12B is a schematic illustration of a second step of the method of FIG. 12A, illustrating extending and elevating the patient's head (for desired neck flexion) to align the pharyngeal axis (PA) and laryngeal axis (LA) for optimal laryngeal visualization.
Figure 12C:
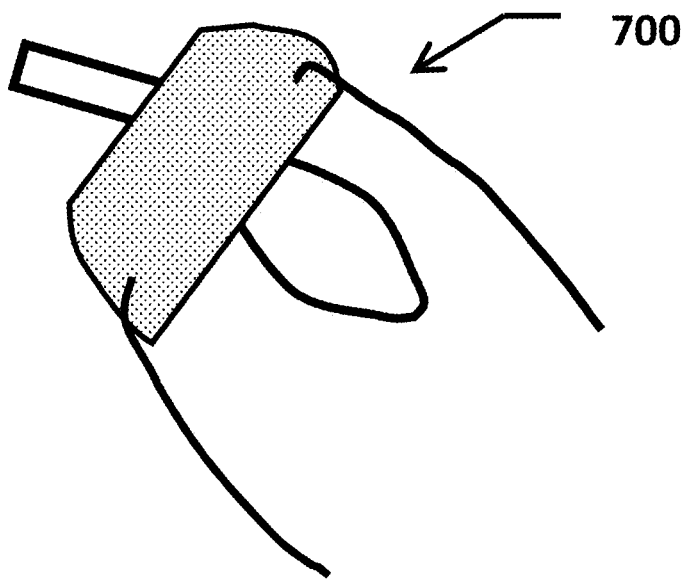
FIG. 12C is a schematic illustration of a third step of the method of FIG. 12A, showing the advancement of the laryngeal airway mask through a balloon-sealable port in the mask.
Figure 12D:
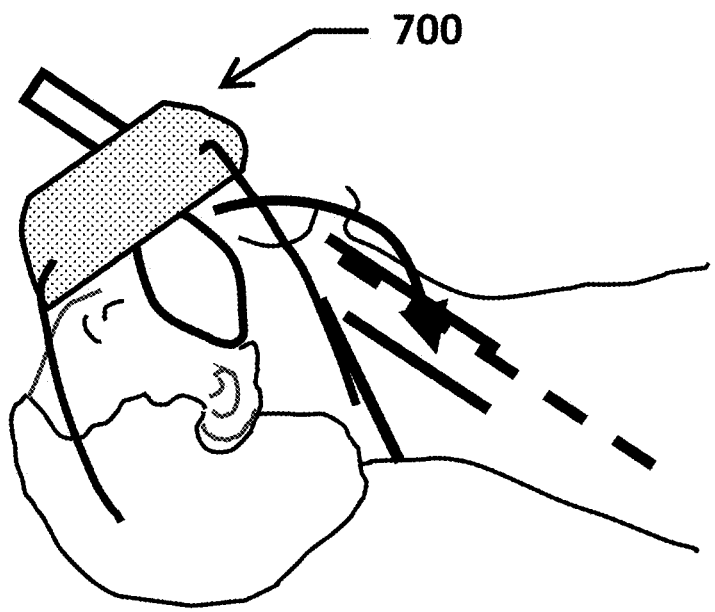
FIG. 12D is a schematic illustration of a fourth step of the method of FIG. 12A, showing the insertion of a distal end of the laryngeal airway mask projecting from one sealed port of the mask into the posterior pharynx (not shown) of the patient to provide oxygenation for short-term ventilation.

In various aspects, the mask system 1000 may be used to facilitate the placement of an LMA in a patient while preventing the release of droplets or aerosolized pathogens from the airway of the patient. FIG. 12A illustrates a patient lying supine with neck in neutral position. When opening the airway, the patient's head is extended and elevated (for desired neck flexion) to align the pharyngeal axis (PA) and laryngeal axis (LA) for optimal laryngeal visualization as illustrated in FIG. 12B. As illustrated in FIG. 12C, an LMA may be positioned within the balloon-sealable port of the mask prior to placement of the LMA in the patient. As illustrated in FIG. 12D, LMA is advanced towards the patient's face and inserted orally. Once the LMA is positioned orally, the mask can be secured around the patient's head while allowing for adequate visualization of the patient's oral airway. Finally, the LMA is fully advanced and positioned in the posterior pharynx (not shown) to provide oxygenation for short-term ventilation. Once the mask is secured, an air-tight seal may be maintained to prevent the release of droplets and aerosolized pathogens from the patient during placement and use of the LMA.

Figure 13A:
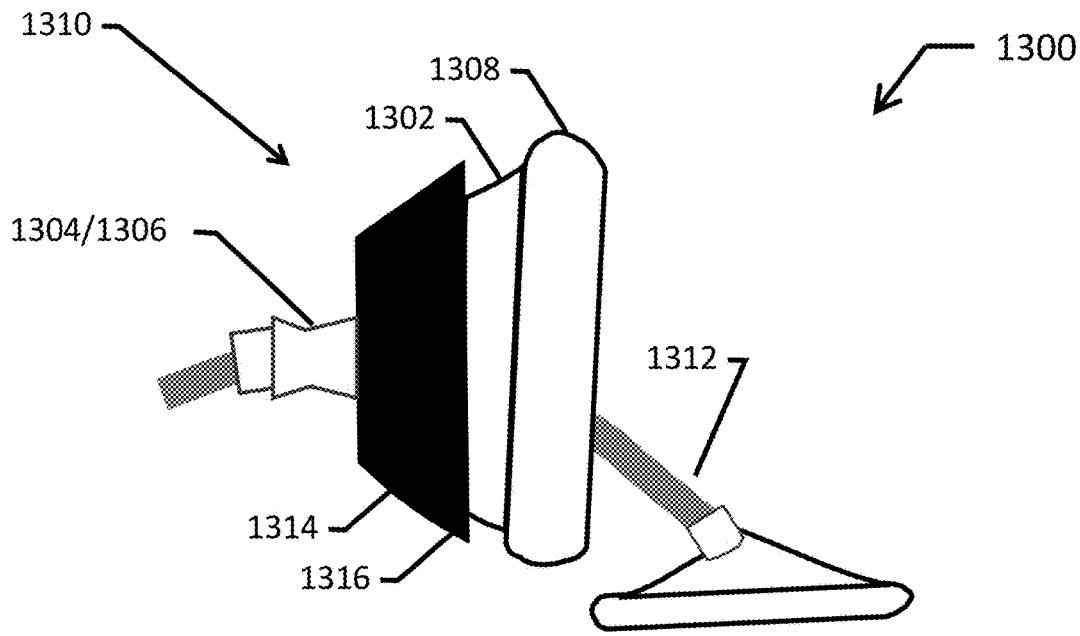
FIG. 13A is a schematic illustration of a quick-seal laryngeal airway device (LAD) in a collapsed configuration in accordance with an aspect of the disclosure.

In various additional aspects, a Quick-Seal LMA device 1300 is disclosed, as shown illustrated in FIG. 13A. The device 1300 includes a patient-fitted mask frame 1302 and an inlet port 1304 containing a frictionless, balloon-sealable valve 1306 similar to the balloon-sealable valves described above. The inlet port 1304 is configured to accommodate the insertion and retention of an LMA 1312 including, but not limited to, any first-generation or second-generation LMAs. In some aspects, the device 1300 may further include a selectively inflatable cushion 1308 attached around the perimeter of a proximal surface of the mask frame 1302 to provide an airtight seal on the face of the patient (not shown) once the device 1300 is secured in place.

Figure 13B:
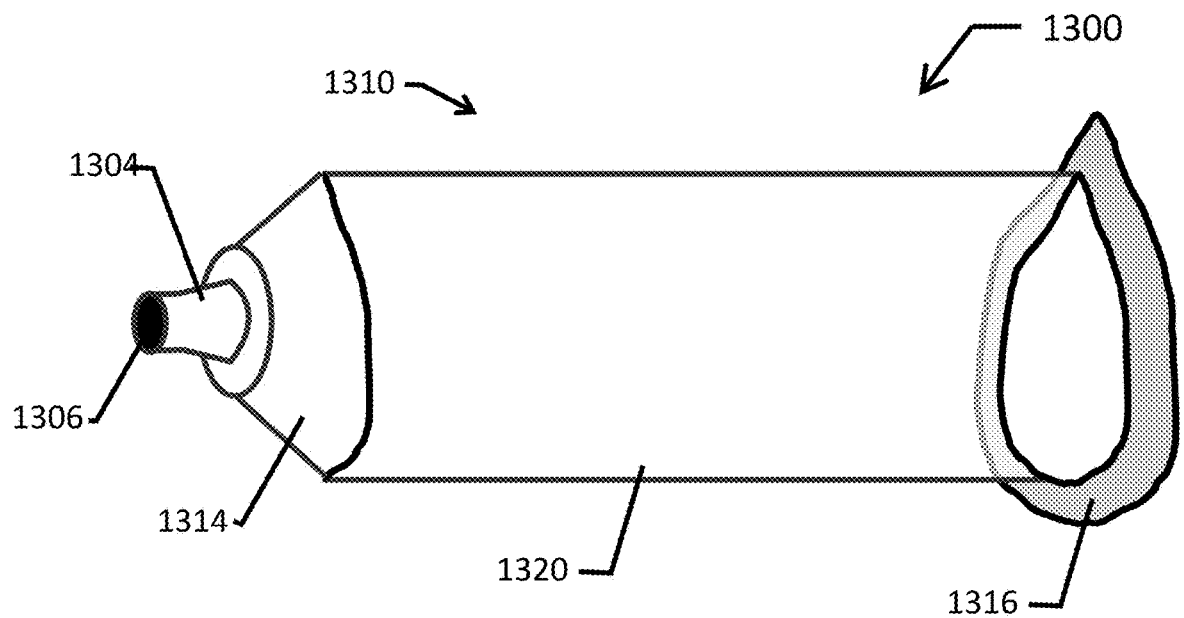
FIG. 13B is a schematic illustration of the LAD of FIG. 13A in an extended configuration in accordance with an aspect of the disclosure.

Referring to FIGS. 13A and 13B, the device 1300 further includes a collapsible insertion channel 1310, which allows for enhanced visibility, user dexterity, and manual adjustment to facilitate successful LMA placements as compared to existing LMA placement devices. The insertion channel 1310 is illustrated in a collapsed configuration in FIG. 13A and in an extended configuration in FIG. 13B. The channel 1310 includes a flexible tubular membrane 1320 coupled to a distal support 1314 and a mask fitting 1316 at opposed distal and proximal ends of the flexible tubular membrane 1320, respectively. The distal support 1314 houses the inlet port 1304 and balloon-sealable valve 1306. The mask fitting 1316 is coupled to the distal surface of the mask frame 1302 to form an airtight seal against the mask frame 1302.

Figure 14A:
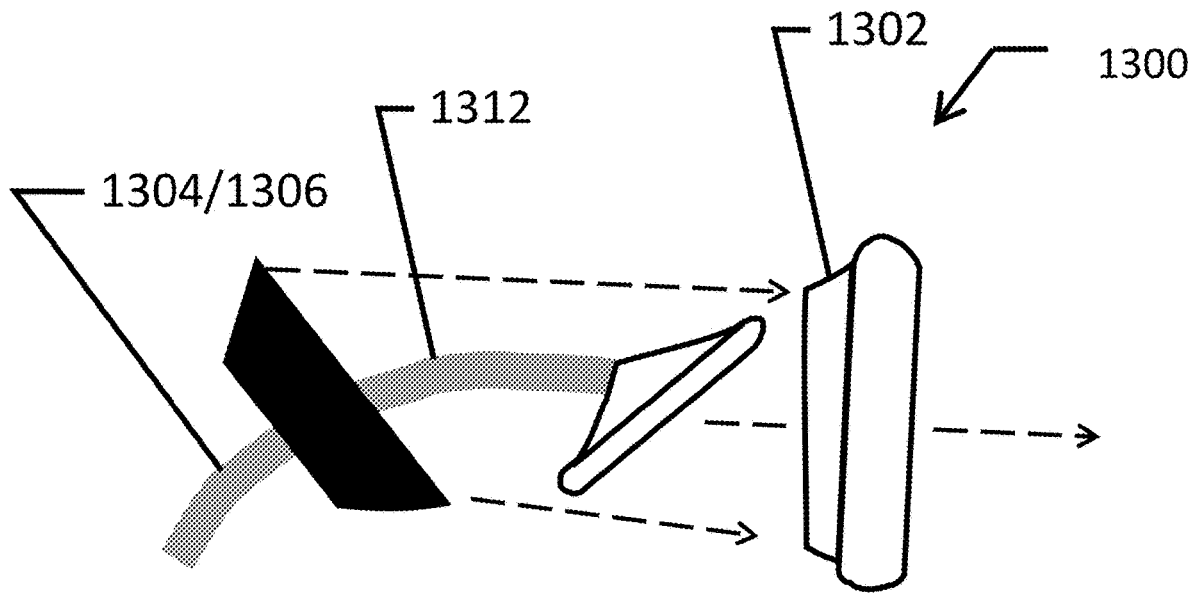
FIG. 14A is a schematic illustration of a first step in a method of placing a laryngeal airway mask in a patient using the quick-seal LAD of FIGS. 13A and 13B, showing insertion of the laryngeal airway mask through a dynamically sealed valve with the LAD in an extended position (collapsible channel not shown).
Figure 14B:
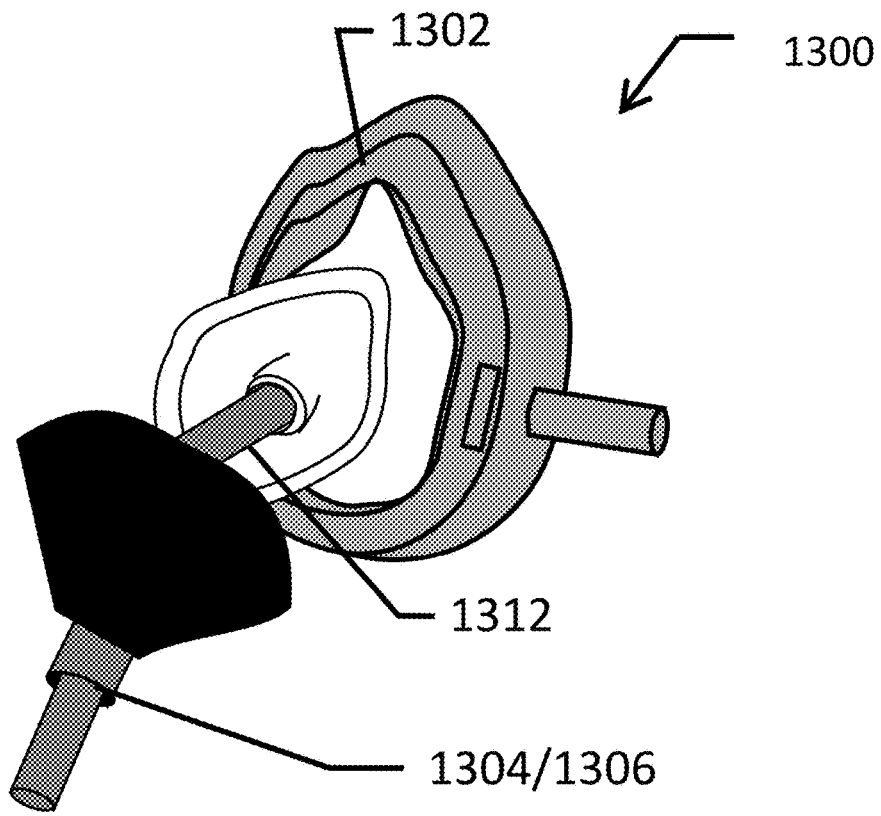
FIG. 14B is a perspective view of the schematic illustration of FIG. 14A.
Figure 14C:
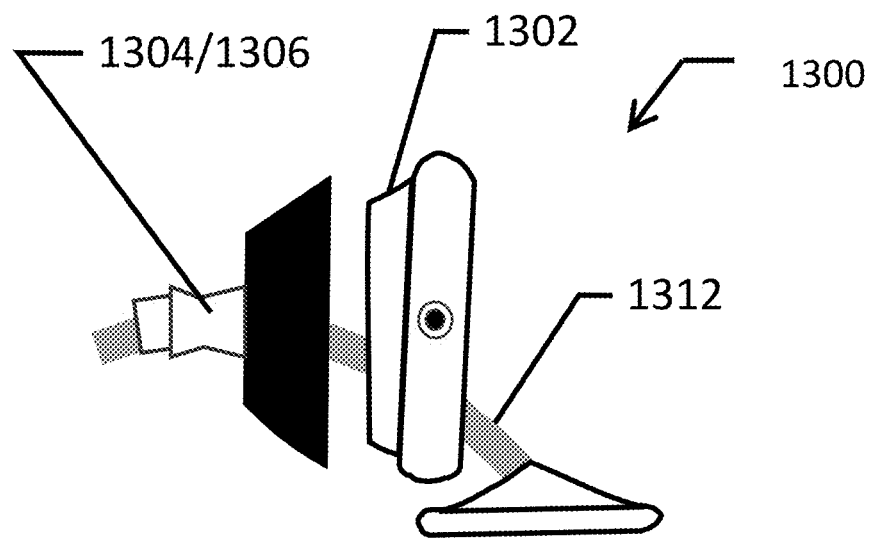
FIG. 14C is a schematic illustration of a second step in the method of placing the laryngeal airway mask using the LAD, showing the insertion of the laryngeal airway mask into the patient while transitioning the LAD from an extended to a collapsed configuration (collapsible channel not shown).
Figure 14D:
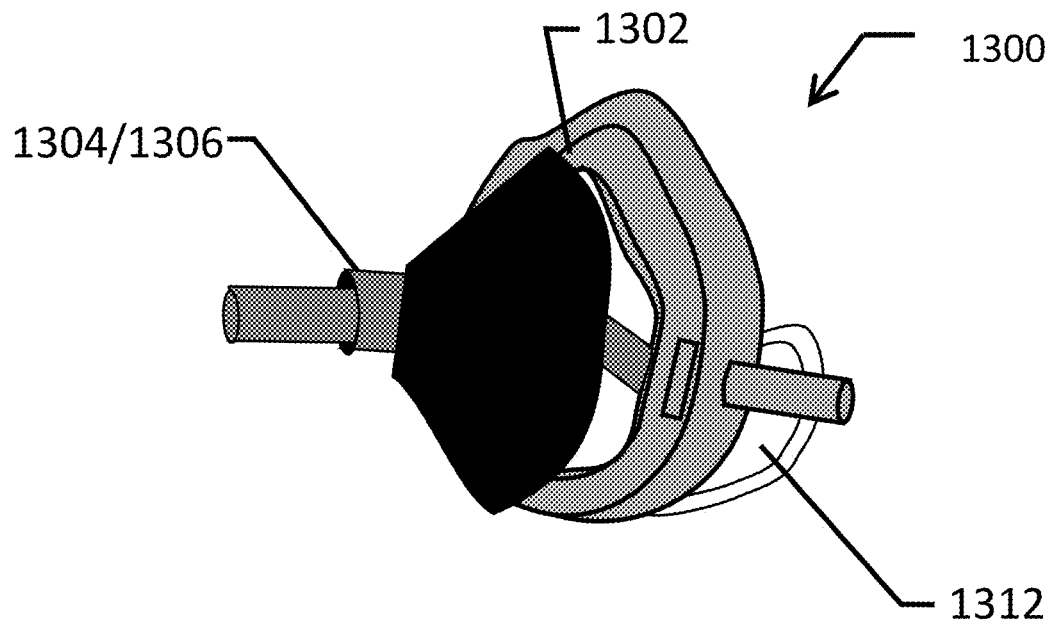
FIG. 14D is a perspective view of the schematic illustration of FIG. 14C.

In the collapsed configuration of the insertion channel 1310, shown illustrated in FIG. 13A, the flexible tubular membrane 1320 is collapsed between the distal support 1314 and the mask fitting 1316. In some aspects, the distal support 1314 and the mask fitting 1316 reversibly couple to retain the insertion channel 1310 in the collapsed configuration. In some aspects, the distal surface of the mask frame 1302 and the mask fitting 1316 may be provided with interlocking mechanical elements that cooperatively interlock or mesh to reversibly couple the mask frame 1302 and the mask fitting 1316. In the extended configuration of the insertion channel 1310, shown illustrated in FIG. 13B, the flexible tubular membrane 1320 is extended between the distal support 1314 and the mask fitting 1316, which is decoupled from the mask frame 1302. FIGS. 14A and 14B illustrate the device 1300 with the insertion channel 1310 (not illustrated) in an extended configuration with an LMA 1312 inserted through the inlet port 1304 and balloon-sealable valve 1306. FIGS. 14C and 14D illustrate the device 1300 with the insertion channel 1310 (not illustrated) in a nearly-collapsed configuration with an LMA 1312 inserted through the inlet port 1304 and balloon-sealable valve 1306 as well as the mask frame 1302 and full length of the insertion channel 1310.

The option to select from a wide variety of LMAs allows for both noninvasive and invasive modalities of ventilation to be performed in COVID-positive patients. The Quick-Seal LMA device has unique design attributes as described above for maintaining a closed airway system and manipulating the enclosed space that sets it apart from all other airway management devices. A variety of advantageous features of the disclosed Quick-Seal LMA device are summarized in Table 1 below.

TABLE 1

| Quick-Seal LMA Features and Benefits | | |
| --- | --- | --- |
| Design Attribute | Clinical Benefits | |
| Inlet Valve Diameter | Compatible with first and second-generation supraglottic airway devices | Full range of device compatibility including ILMA (largest) to classic LMA (standard size) |
| Balloon-Sealed Valve | Allows dynamic sealing of a single access port in situ | Deflated for insertion of LMA device and inflated to establish an airtight seal |
| Inflatable Mask Cushion | Allows for optimal comfort and fit to patient's face | Allows for a dynamic surface to seal to a wide range of facial contours |
| Collapsible Channel | Allows for physical manipulation of enclosed space without compromising the airtight seal | Allows for manual insertion of fingers (exterior) and maneuvering of the LMA device (interior) to guide proper LMA placement |
| Versatility | Allows for multipurpose use in various clinical indications | Allows for interchangeable use of invasive and non-invasive ventilation modalities |
| Protective | Allows for continuous high-pressure ventilation within a closed airway system | Reduces risk of droplet and aerosol particle dispersion from patient airways |

The Quick-Seal LMA device is well suited for clinical use and provider protection during rapid stabilization in the field, during out-of-hospital airway management, and during transportation of persons with known or suspected COVID-19. Additionally, the use of the Quick-Seal LMA in critically ill patients provides a conduit for quick and easy intubation through the LMA without compromising the closed airway system.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

Any publications, patents, patent applications, and other references cited in this application are incorporated herein by reference in their entirety for all purposes to the same extent as if each individual publication, patent, patent application, or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

What is claimed is:

1. A sealed access endotracheal tube adapter configured to attach to an endotracheal tube, the adapter comprising:
   a) an access port comprising a first tube ending in a proximal entry port and a distal endotracheal tube connector, the proximal entry port configured to receive at least medical instrument and the distal endotracheal tube connector configured to couple to a proximal end of the endotracheal tube;
   b) a selectively pressurized balloon-valve seal positioned within an inner surface of the first tube distal to the proximal entry port, the balloon-valve seal comprising at least two balloons attached to at least a portion of the inner surface of the first tube, wherein the balloon-valve seal assumes a sealed configuration when the at least two balloons are inflated and the balloon-valve seal assumes an open configuration when the at least two balloons are deflated; and
   c) a ventilation system connector comprising a second tube comprising a distal end operatively coupled to the first tube between the balloon-valve seal and the distal endotracheal tube connector and a proximal end ending in a ventilation system connector, the ventilation system connector configured to couple to a ventilation device.

2. The adapter of claim 1, wherein the at least one medical instrument is selected from a bronchoscope and a laryngoscope.

3. The adapter of claim 1, wherein each balloon of the at least two balloons comprises an elastic membrane, wherein the elastic membrane and an underlying portion of the inner surface of the first tube define an inflatable volume.

4. The adapter of claim 3, wherein the elastic membrane comprises an elastic polymer selected from latex, silicone, and rubber.

5. The adapter of claim 4, wherein each elastic membrane of each of the balloons further comprises a low-friction outer surface.

6. The adapter of claim 5, wherein the low-friction outer surface comprises a hydrophilic coating.

7. The adapter of claim 6, further comprising an inflation port operatively connected to each of the inflatable volumes of each of the balloons, the inflation port configured to transfer a fluid into each of the inflatable volumes to inflate and seal the balloon-valve seal and to transfer the fluid out of each of the inflatable volumes to deflate and open the balloon-valve seal.

8. The adapter of claim 7, wherein the fluid is selected from air and saline solution.

9. The adapter of claim 1, further comprising a rubberized diaphragm seal positioned over the proximal entry port of the first tube.

10. The adapter of claim 1, further comprising a layer of a filtration material positioned within the first tube, wherein the filtration material is proximal to the balloon-valve seal positioned over the proximal entry port of the first tube.

11. An intubation mask system, comprising:
   a) a mask comprising at least one central opening, the least one central openings defining at least one adjacent, noncontiguous port, wherein each of the ports is configured to receive at least one medical instrument:
   b) at least one balloon-valve seal, each balloon-valve seal positioned within each of the at least one ports, each balloon-valve seal comprising at least two balloons, wherein the balloon-valve seal assumes a sealed configuration when the at least two balloons are inflated and the balloon-valve seal assumes an open configuration when the at least two balloons are deflated; and
   c) a scaffold and a plurality of removable head straps, each head strap comprising a first end attached to the mask and a second end attached to the scaffold, wherein the mask, the scaffold, and the plurality of straps are configured to secure to a head of a patient with the mask positioned on the patient's face and the scaffold positioned behind the head of the patient.

12. The system of claim 11, wherein the at least one medical instrument is selected from a bronchoscope, a laryngoscope, an endotracheal tube, a laryngeal mask airway, an orogastric tube, and a nasogastric tube.

13. The system of claim 11, wherein the mask and scaffold comprise at least one stiff biocompatible material selected from PLA (polylactic acid), ABS (acrylonitrile butadiene styrene), copper composite HTPLA (high temperature polylactic acid), and any combination thereof.

14. The system of claim 13, wherein the peripheral seal comprises a biocompatible sealant selected from polypropylene, latex, silicon, and any combination thereof.

15. The system of claim 13, wherein the mask further comprises a clear plastic sheet attached to the mask perimeter, the mask perimeter further comprising a nose bridge and a mask frame containing an internal adjustable wire, wherein the at least one central opening is contained within the clear plastic sheet and the at least one medical instrument comprises a laryngeal mask airway.

16. The system of claim 11, wherein the mask further comprises a mask perimeter and a peripheral seal lining the mask perimeter, the peripheral seal configured to seal to the patient's face and to prevent pressure-induced skin injuries.

17. The system of claim 11, wherein each balloon of the at least two balloons comprises an elastic membrane, the elastic membrane comprising an elastic polymer selected from latex, silicone, and rubber.

18. The system of claim 17, wherein each elastic membrane of each balloon further comprises a low-friction outer surface comprising a hydrophilic coating.

19. A quick-seal laryngeal mask airway-specific system, comprising a) a patient-fitted mask frame defining a central opening;
b) a selectively inflatable cushion coupled to a proximal surface of the mask frame, the cushion configured to seal against a patient's face;
c) a collapsible insertion channel comprising a flexible tubular membrane comprising a proximal end and a distal end, a mask fitting coupled to the proximal end of the flexible tubular membrane, and an inlet port attached to the distal end of the flexible tubular membrane, where
   i) the mask fitting is further coupled to a distal surface of the mask frame;
   ii) the inlet port is configured to receive at least one of a laryngoscope and at least a portion of a laryngeal mask airway device;
   iii) the insertion channel is configured to assume an extended configuration wherein the flexible tubular membrane is extended distally between the inlet port and the mask fitting and the insertion channel is further configured to assume a collapsed configuration wherein the inlet port is reversibly coupled to the mask fitting with the flexible tubular membrane stowed therebetween, and
d) a balloon-valve seal positioned within the inlet port, the balloon-valve seal comprising at least two balloons, each balloon having a low-friction surface, wherein the balloon-valve seal assumes a sealed configuration when the at least two balloons are inflated and the balloon-valve seal assumes an open configuration when the at least two balloons are deflated.

20. The system of claim 19, wherein each balloon of the at least two balloons comprises an elastic membrane, the elastic membrane comprising an elastic polymer selected from latex, silicone, and rubber, the elastic membrane further comprising a low-friction hydrophilic coating.

* * * * *